US006452065B2

(12) United States Patent
Zheng et al.

(10) Patent No.: US 6,452,065 B2
(45) Date of Patent: *Sep. 17, 2002

(54) TRANSGENIC MOUSE EXPRESSING NON-NATIVE WILD-TYPE AND FAMILIAL ALZHEIMER'S DISEASE MUTANT PRESENILIN 1 PROTEIN ON NATIVE PRESENILIN 1 NULL BACKGROUND

(75) Inventors: Hui Zheng, Edison; Ping Jiang, Trenton; Su Qian, Sayreville; Leonardus H. T. Van Der Ploeg, Scotch Plains, all of NJ (US); Philip Chun-Ying Wong, Timonium, MD (US); Sangram S. Sisodia, Chicago, IL (US)

(73) Assignees: Merck & Co., Inc., Rahway; Johns Hopkins University, Baltimore, both of NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/078,871

(22) Filed: May 14, 1998

Related U.S. Application Data

(60) Provisional application No. 60/078,465, filed on Mar. 18, 1998, and provisional application No. 60/046,488, filed on May 14, 1997.

(51) Int. Cl.[7] ........................ A01K 67/00; A01K 67/033; A01K 67/027; C12N 15/00; C12Q 1/02
(52) U.S. Cl. ..................... 800/12; 3/18; 3/22; 3/25; 435/29; 435/354
(58) Field of Search .................. 800/9, 12, 14, 800/18, 22, 25, 3; 435/354

(56) References Cited

U.S. PATENT DOCUMENTS 6,284,944 B1 * 9/2001 Scott et al. .................. 800/3

FOREIGN PATENT DOCUMENTS

WO    WO 96/06927    * 7/1996

OTHER PUBLICATIONS

Sherrington et al (1995) Nature 375, 754–760.*
Green et al (1994) Nature Genetics 7, 13–21.*
Conlon, et al., "Notch 1 is required for the coordinate segmentation of somites", Development, vol. 121, pp. 1533–1545, 1995.
Games, et al., "Alzheimer–type neuropathology in transgenic mice overexpressing V717F β–amyloid precursor protein", Nature, vol. 373, Feb. 9, 1995, pp. 523+527.
Hrabe de Angelis, "Maintenance of somite borders in mice requires the Delta homologue DIl1", Nature, vol. 386, Apr. 17, 1997, pp. 717–721.

Levitan, et al., "Fecilitation of lin–12–mediated signalling by sel–12, a *Caenorhabditis elegans* S182 Alzheimer's . . .", Nature, vol. 377, Sep. 28, 1995, pp. 351–354.
Cruts, et al., "The presenilin genes: a new gene family involved in Alzheimer disease pathology", Human Molecular Genetics, vol. 5, 1996, pp. 1449–1455.
Gravina, et al., "Amyloid β Protein (Aβ) in Alzheimer's Disease Brain", J. of Biol. Chem., vol. 270, No. 13, Mar. 31, 1995, pp. 7013–7016.
Gordon, et al., "Regulation of Thy–1 Gene Expression in Transgenic Mice", Cell, vol. 50, Jul. 31, 1987, pp. 445–452.
Wagner, "On Transferring Genes Into Stem Cells and Mice", EMBO J., vol. 9, No. 10, pp. 3025–3032, 1990.
Kollias, et al., "Differential regulation of a Thy–1 gene in transgenic mice", Proc. Natl. Acad. Sci. USA, vol. 84, pp. 1492–1496, Mar. 1987.
Lemere, et al., "The E280A presenilin 1 Alzheimer mutation produces increased Aβ42 deposition . . . ", Nature Medicine, vol. 2, No. 10, Oct. 10, 1996, pp. 1146–1150.
Mansour, et al., "Disruption of the proto–oncogene int–2 in mouse embryo–derived stem cells: a general strategy . . . ", Nature, vol. 336, Nov. 24, 1988, pp. 348–352.
van Rus, et al., "Chromosomal localization of the human Thy–1 gene", Proc. Natl. Acad. Sci. USA, vol. 82, pp. 5832–5835, Sep. 1985.
Selkoe, et al., "Alzheimer's Disease: Genotypes, Phenotype and Treatments", Science, vol. 275, pp. 630–631 (1997).
Bradley, et al., "Production and analysis of chimeric mice. In Teratocinomas and Embryonic . . .", E. J. Robertson, ed. Oxford: IRL Press, (1987), pp. 113–151.
Sirinathsinghji, et al., "Imaging gene expression in neural grafts", in Molecular Imaging in Neuroscience, Sharif eds., pp. 43–70, Oxford University Press, New York, 1993.
Robertson, "Teratocarcinomas and embryonic stem cells", IRL Press, pp. 71–112, 1987.
Capecchi, et al., "The New Mouse Genetics: Altering the Genome by Gene Targeting", Trends in Genetics, Mar. 1989, vol. 5, No. 3, pp. 70–76.
Hsiao, et al., "Correlative Memory Deficits, Aβ Elevation, and Amyloid Plaques in Transgenic Mice", Science, vol. 274, Oct. 4, 1996, pp. 99–102.

(List continued on next page.)

Primary Examiner—Deborah Crouch
(74) Attorney, Agent, or Firm—Michael D. Yablonsky; Jack L. Tribble

(57) ABSTRACT

The present invention relates to a transgenic non-human animal embryo lacking native presenilin 1 and a transgenic non-human animal having only a non-native presenilin 1. The transgenic animals and cells derived therefrom can be used in the study of the expression pattern, activity and modulators of presenilin 1, in the study of the role of presenilin 1 in Alzheimer's Disease and in the study of disorders of the central nervous system.

29 Claims, 14 Drawing Sheets

OTHER PUBLICATIONS

Artavanis–Tsakonas, et al., Notch Signaling, Science, vol. 268, Apr. 14, 1995, pp. 225–232.

Gossler, et al., "Transgenesis by means of blastocyst–derived embryonic stem cells lines", Proc. Natl. Acad. Sci. USA, vol. 83, 99. 9065–9069, Dec. 1986.

Bradley, et al., "Formation of germ–line chimaeras from embryo–derived teratocarcinomas cell lines", Nature, vol. 309, pp. 255–258 (1984).

Jaenisch, "Transgenic Animals", Science, vol. 240, pp. 1468–1474 (1988).

Glenner, et al., "Alzheimer's Disease: Initial Report of the Purification and Characterization of a Novel . . . ", vol. 120, No. 3, pp. 885–890, 1984.

Thomas, et al., "Site–Directed Mutagenesis by Gene Targeting in Mouse Embryo–Derived Stem Cells", Cell, vol. 51, pp. 503–512, Nov. 6, 1987.

Frohman, et al., "Cut, Paste, amd ave: New Approaches to Altering Specific Genes in Mice", Cell, vol. 56, pp. 145–147, Jan. 27, 1989.

Reneker, et al., TGFα can act as a chemoattractant to perioptic mesenchymal cells in developing mouse eyes, Development, vol. 121, 1669–1680, 1995.

Levitan, et al., "Assesment of normal and mutant human presenilin function in Caenorhabditis . . . ", Proc. Natl. Acad. Sci. USA, vol. 93, pp. 14940–14944, Dec. 1996.

Robertson, et al., "Germ–line transmission of genes introduced into cultured pluropotential cells by retroviral vector", Nature, vol. 323, Oct. 2, 1986, pp. 445–448.

Evans, et al., "Establishment in culture of pluripotential cells from mouse embryos", Nature, vol. 292, Jul. 9, 1981, pp. 154–156.

Citron, et al., "Mutant presenilins of Alzheimer's disease increase production of 42–residue amyloid β–protein . . .", Nature Medicine, vol. 3, No. 1, Jan. 1997, pp. 67–72.

Shen, et al., "Skeletal and CNA Defects in Presenilin–1–Deficient Mice", Cell, vol. 89, May 16, 1997, pp. 629–639.

Wong, et al., "Presenilin 1 is required for Notch 1 and Dll1 expression in the paraxial mesoderm", Nature, vol. 387, May 15, 1997, pp. 288–292.

Scheuner, et al., et al., "Secreted amyloid β–protein similar to that in the senile plaques of Alzheimer's disease . . . ", Nature Medicine, vol. 2, No., 8, Aug. 1996, pp. 864–870.

Qian, et al., "Mutant Human Presenilin 1 Protects presenilin 1 Null Mouse against Embryonic Lethality . . . ", Neuron, vol. 20, pp. 611–617, Mar. 1998.

Holcomb, et al., "Accelerated Alzheimer–type phenotype in transgenic mice carrying both mutant amyloid precursor . . .", Nature Medicine, vol. 4, No. 1, Jan. 1998, pp. 97–100.

Duff, et al., "Increased amyloid–β42(43) in brains of mice expressing mutant presenilin 1", Nature, vol. 383, Oct. 24, 1996, pp. 710–713.

De Strooper, et al., "Deficiency of presenilin–1 inhibits the normal cleavage of amyloid precursor protein", Nature, vol. 391, Jan. 22, 1998, pp. 387–390.

Davis, et al., "An Alzheimer's Disease–Linked PS1 Variant Rescues the Developmental Abnormalities . . . ", Neuron, vol. 20, pp. 603–609, Mar. 1998.

Borchelt, et al., "Familial Alzheimer's Disease–Linked Presenilin 1 Variants Elevate Aβ1–42/1–40 . . .", Neuron, vol. 17, pp. 1005–1013, Nov., 1995.

Zheng, et al., "β–Amyloid Precursor Protein–Deficient Mice Show Reactive Gliosis and Decreased Locomotor Activity", Cell, vol. 81, pp. 525–531, May 19, 1995.

Sahara, et al., "Identification and characterization of presenilin I–467, I–463 and I–374", FEBS Letters, vol. 381, 1996, pp. 7–11.

Borchet, et al., "Accelerated Amyloid Deposition in the Brains of Transgenic Mice Coexpressing Mutant . . . ", Neuron, vol. 19, pp. 939–945, Oct. 1997.

Thinakaran, et al., "Endoproteolysis of Presenilin 1 and Accumulation of Processed Derivatives in Vivo", Neuron, vol. 17, pp. 181–190, Jul. 1996.

Baribault, et al., "Embryonic Stem Cells Culture and Gene Targeting in Transgenic Mice", Mol. Biol. Med., vol. 6, 1989, pp. 481–492.

Southern, et al., "Transformation of Mammalian Cellls to Antibiotic Resistance with a Bacterial Gene Under Control . . . ", J. of Mol. and Appl. Genet., vol. 1, pp. 327–341, 1982.

Bradley, et al., "Modifying the Mouse: Design and Desire", Bio/Technology, vol. 10, May 1992, pp. 534–539.

* cited by examiner

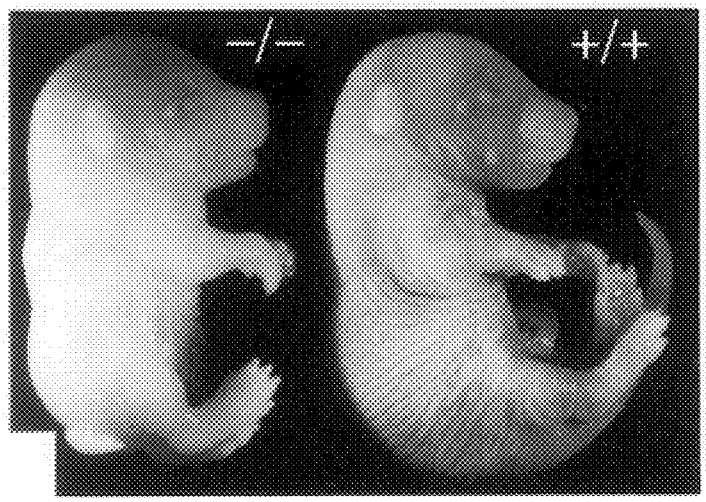
FIG.2A  FIG.2B
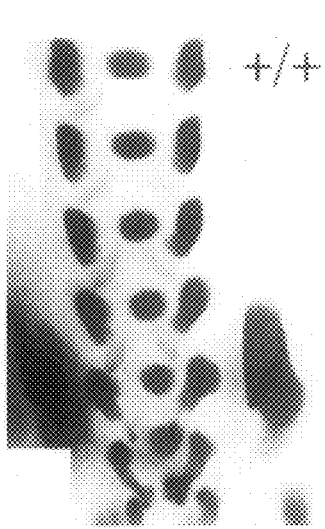
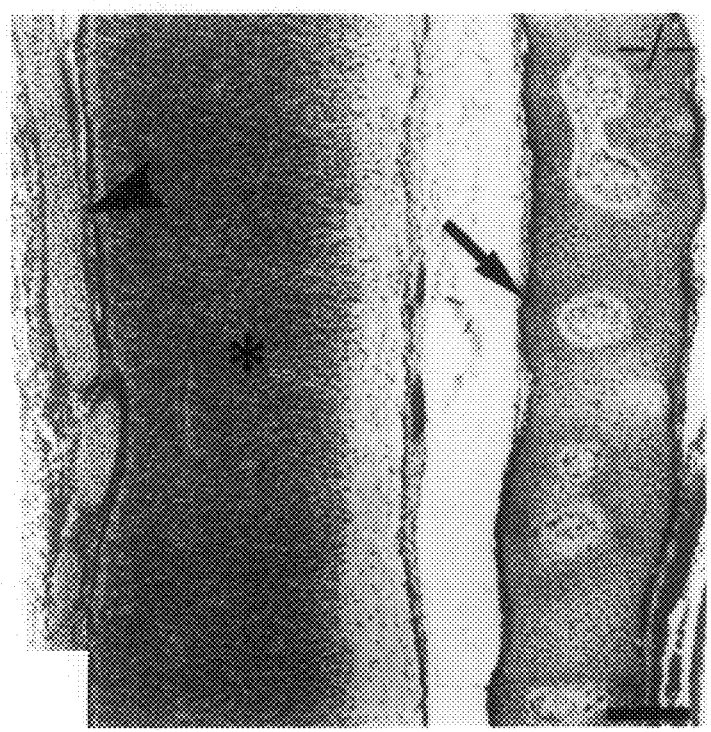
FIG.2C  FIG.2D

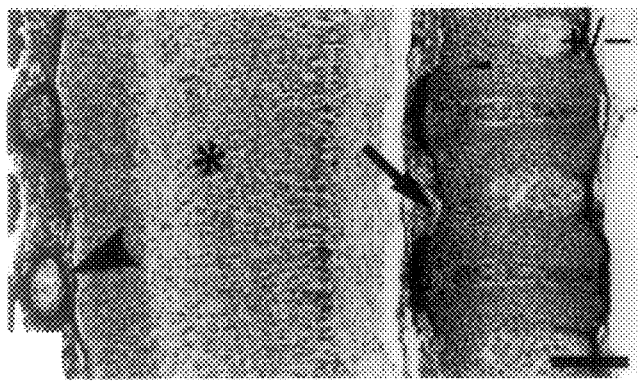
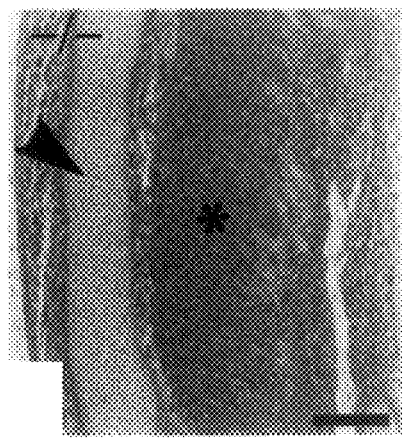
FIG.2E  FIG.2H
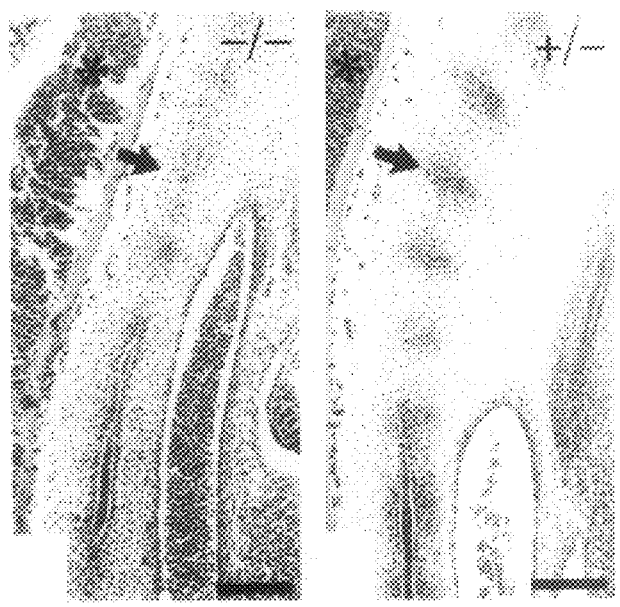
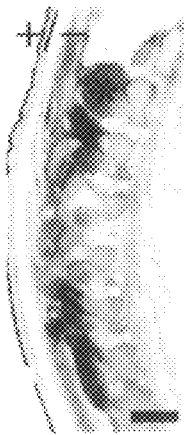
FIG.2F  FIG.2G  FIG.2I

ADULT BRAIN AREAS

TRANSGENIC MOUSE EXPRESSING NON-NATIVE WILD-TYPE AND FAMILIAL ALZHEIMER'S DISEASE MUTANT PRESENILIN 1 PROTEIN ON NATIVE PRESENILIN 1 NULL BACKGROUND

CROSS-REFERENCE TO RELATED APPLICATIONS

This application is entitled to the benefit of U.S. provisional application 60/078,465, filed Mar. 18, 1998, and U.S. provisional application 60/046,488 filed May 14, 1997.

STATEMENT REGARDING FEDERALLY-SPONSORED R&D

This invention was made in part with federally-sponsored research. The U.S. Government has certain rights in this invention.

REFERENCE TO MICROFICHE APPENDIX

Not applicable.

FIELD OF THE INVENTION

The present invention relates to a transgenic non-human animal lacking native presenilin 1 (PS1) protein and a transgenic non-human animal expressing either the wild-type human PS1 or human PS1 containing a Familial Alzheimer's Disease (FAD) mutation on native PS1 null background. The transgenic animal can be used in the study of the in vivo functions of PS1 and the effect of FAD mutation in PS1 function both during embryonic development and during aging. The transgenic animal can also be used in the identification of compounds that modulate the expression or activity of PS1.

BACKGROUND OF THE INVENTION

Presenilin 1 (PS1) is a protein expressed in the central nervous system as well as other tissues of animals from early embryonic development through adult life. Endoproteolytically processed in vivo, (G. Thinakaran et al., Neuron 17:181 (1996)), PS1 is an eight transmembrane protein homologous to sel-12, a *C. elegans* protein that facilitates signaling mediated by the Notch/in-12 family of receptors (D. Levitan & I. Greenwald, Nature, 377:351 (1995), S. Artavanis-Tsakonas et al., Science 268:225 (1995)). In nematodes, particular egg-laying defects associated with loss of sel-12 function are rescued by PS1 (D. Levitan et al., Proc. Natl. Acad. Sci., USA 93:14940 (1996)), indicating that for some functions, the homologous proteins might be functionally interchangeable.

PS1 has been linked in Alzheimer's Disease (AD), a neurological disorder that disproportionately affects the population over 65 years of age. Mutations in PS1 contribute to approximately 25% of early-onset familial Alzheimer's Disease. Incidence of the disease increases from less than 1% at age 60–65, to 5% at age 75, to as high as 47% at age 85. As a result, 60% to 80% of all cases of dementia in persons over age 65 are caused by AD. Afflicted individuals exhibit impaired cognitive function and memory.

Distinguishing features of AD include the presence of senile plaques as well as, neurofibrillary tangles and extensive neuronal loss in the neocortex, hippocampus and associated structures. The senile plaques are extracellular deposits of heterogeneous substances of which the major component is a 39–43 amino acid peptide referred to as β-amyloid peptide or Aβ(Glenner and Wong,Biochem. Biophys. Res. Commun. 120:885–890 (1984). The 4 kDa Aβ peptide is derived by proteolytic cleavage of a larger β-amyloid precursor protein (APP). The plaques are surrounded by a halo of dystrophic neurites, glia and astrocytes. β-amyloid deposits are also present in neocortex blood vessel walls. Other components of the plaques include ubiquitin, amyloid P, Apo E, interleukin-1, and a-i-antichymotrypsin. Although the complete etiology of AD has not yet been determined, much is now known, including genetic, immunological and environmental factors implicated in the development of AD.

Genetic data is seen from the study of familial AD. Although the majority of AD cases appear sporadic, about 10% of cases are early onset familial AD (FAD). Genetic analysis of FAD families has established that the disorder is associated with autosomal dominant inheritance of mutations in specific genes including the β-amyloid precursor protein (APP) located on chromosome 21, the PS1 gene on chromosome 14 and a homolog of PS1, presenilin 2 (PS2), located on chromosome 1. About 25% of the early-onset FAD cases are linked to mutations in PS1. Biochemical studies have shown that mutations in all three genes lead to an increased production of either the total Aβ or Aβ42(43), which is believed to be more amylodogenic (Scheuner et al., Nature Medicine 2:864–870 (1996); Selkoe, Science, 275:630–631 (1997)). To date, 42 different missense mutations and one in-frame splice site mutation were described (Cruts et al, Hum. Mol. Genet. 5:1449–1455 (1996)). However, neither all of the physiological roles of PS1, nor its mechanism in AD pathogenesis, are fully understood at this time.

Transgenic non-human animal technology offers a model system to address the effects of genes associated with AD. Addition of a gene construct directing the expression of human PS1 or its components to key regions in the central nervous system provide a means to study the expression and activity of PS1 and modulators of PS1. Previous attempts to express either the wild-type human PS1 protein or human PS1 containing various FAD mutations under either the PDGF promoter or the PrP promoter have been reported (Duff et al., Nature 383:710–713 (1996); Borchelt et al., Neuron 17:1005–1013 (1996)). In each case, the PS1 transgenes were reportedly expressed on the wild-type murine PS1 background. Thus, a mixture of murine and human PS1 proteins were produced in the resulting transgenic mice.

A relative increase of Aβ42(43) level has been observed in plasma and fibroblast cell cultures derived from PS1 FAD subjects and in transgenic mice expressing human PS1 FAD proteins (Scheuner et al, 1996; Duff et al., (1996); Borchelt et al, (1996); Lemere et al., (1996); Citron et al., Nature Medicine 3:67–72 (1997)). That result suggests that the pathogenic consequence of PS1 mutations might be through APP processing and Aβ42(43) production.

SUMMARY OF THE INVENTION

Accordingly, it is an aspect of this invention to provide a non-human transgenic animals which is heterozygous for a functional PS1 gene native to that animal. As used herein, functional is used to describe a gene or protein that, when present in a cell or in vitro system, performs normally as if in a native or unaltered condition or environment. The animal of this aspect of the invention is useful for the study of the tissue and temporal specific expression or activity of PS1 in an animal having only one functional copy of the gene. The animal is also useful for studying the ability of a variety of compounds to act as modulators of PS1 activity or expression in vivo or, by providing cells for culture, in vitro. As used herein, a modulator is a compound that causes a change in the expression or activity of PS1, or causes a change in the effect of the interaction of PS1 with its ligand(s), or other protein(s). In an embodiment of this aspect, the animal is used in a method for the preparation of a further animal which lacks a functional native PS1 gene. In another embodiment, the animal of this aspect is used in a method to prepare an animal which expresses a non-native PS1 gene in the absence of the expression of a native PS1 gene. In particular embodiments the non-human animal is a mouse. In further embodiments the non-native PS1 is a wild-type human PS1, an A246E mutant human PS1 gene or any other mutant human PS1 gene.

In reference to the transgenic animals of this invention, we refer to transgenes and genes. As used herein, a transgene is a genetic construct including a gene. The transgene is integrated into one or more chromosomes in the cells in an animal by methods known in the art. Once integrated, the transgene is carried in at least one place in the chromosomes of a transgenic animal. A gene is a nucleotide sequence that encodes a protein. The gene and/or transgene may also include genetic regulatory elements and/or structural elements known in the art.

Another aspect of the invention is a non-human animal embryo deficient for native PS1 expression. This embryo is useful in studying the effects of the lack of presenilin 1 on the developing animal. In particular embodiments the animal is a mouse. The animal embryo is also useful as a source of cells lacking a functional native PS1 gene. The cells are useful in in vitro culture studies in the absence of PS1.

An aspect of this invention is a method to obtain an animal in which the cells lack a functional gene PS1 native to the animal. The method includes providing a gene for an altered form of the PS1 gene native to the animal in the form of a transgene and targeting the transgene into a chromosome of the animal at the place of the native PS1 gene. The transgene can be introduced into the embryonic stem cells by a variety of methods known in the art, including electroporation, microinjection, and lipofection. Cells carrying the transgene can then be injected into blastocysts which are then implanted into pseudopregnant animals. In alternate embodiments, the transgene-targeted embryonic stem cells can be coincubated with fertilized eggs or morulae followed by implantation into females. After gestation, the animals obtained are chimeric founder transgenic animals. The founder animals can be used in further embodiments to cross with wild-type animals to produce F1 animals heterozygous for the altered PS1 gene. In further embodiments, these heterozygous animals can be interbred to obtain the non-viable transgenic embryos whose somatic and germ cells are homozygous for the altered PS1 gene and thereby lack a functional PS1 gene. In other embodiments, the heterozygous animals can be used to produce cells lines. In preferred embodiments, the animals are mice.

A further aspect of the present invention is a transgenic nonhuman animal which expresses a non-native PS1 on a native PS1 null background. In particular embodiments, the null background is generated by producing an animal with an altered native PS1 gene that is non-functional, i.e. a knockout. The animal can be heterozygous (i.e., having a different allelic representation of a gene on each of a pair of chromosomes of a diploid genome) or homozygous (i.e., having the same representation of a gene on each of a pair of chromosomes of a diploid genome) for the altered PS1 gene and can be hemizygous (i.e., having a gene represented on only one of a pair of chromosomes of a diploid genome) or homozygous for the non-native PS1 gene. In preferred embodiments, the animal is a mouse. In particular embodiments the non-native PS1 gene can be a wild-type or mutant allele including those mutant alleles associated with a disease. In further embodiments, the non-native PS1 is a human PS1. In particular embodiments the PS1 gene is a human wild-type PS1 allele, the human A246E mutant allele or another mutant human PS1. In further embodiments the non-native PS1 gene is operably linked to a promoter. As used herein, operably linked is used to denote a functional connection between two elements whose orientation relevant to one another can vary. In this particular case, it is understood in the art that a promoter can be operably linked to the coding sequence of a gene to direct the expression of the coding sequence while placed at various distances from the coding sequence in a genetic construct. In a preferred embodiment, the promoter is a neuronal specific human Thy-1 promoter. Further embodiments are cells derived from animals of this aspect of the invention.

An aspect of this invention is a method of producing transgenic animals having a transgene including a non-native PS1 gene on a native PS1 null background. The method includes providing transgenic animals of this invention whose cells are heterozygous for a native gene encoding a functional PS1 protein and an altered native PS1 gene. These animals are crossed with transgenic animals of this invention that are hemizygous for a transgene including a non-native PS1 gene to obtain animals that are both heterozygous for an altered native PS1 gene and hemizygous for a non-native PS1 gene. The latter animals are interbred to obtain animals that are homozygous or hemizygous for the non-native PS1 and are homozygous for the altered native PS1 gene. In particular embodiments, cell lines are produced from any of the animals produced in the steps of the method.

The transgenic animals and cells of this invention are useful in the determination of the in vivo function of a non-native PS1 in the central nervous system and in other tissues of an animal. The animals are also useful in studying the tissue and temporal specific expression patterns of a non-native PS1 throughout the animals. The animals are also useful in determining the ability for various forms of wild-type and mutant alleles of a non-native PS1 to rescue the native PS1 null deficiency. The animals are also useful for identifying and studying the ability of a variety of compounds to act as modulators of the expression or activity of a non-native PS1 in vivo, or by providing cells for culture, for in vitro studies.

An aspect of this invention is an assay to detect the effect of a compound on Aβ production. In a preferred embodiment, the assay is performed by providing an animal of the present invention, exposing the animal to the compound, and measuring Aβ production in the animal. The measurement can be compared to a measurement of Aβ production in a genetically similar or identical animal that is not exposed to the compound. In another preferred embodiment, the assay is conducted as above except that one uses populations of cells derived from an animal of this invention in place of the animals themselves. In conducting the assays of this invention, the animals or cells are exposed to compounds at various dosages over various periods of time. The effect of a compound on Aβ production can be measured by a variety of methods known to those of skill in the art including sandwich ELISA, western blot analysis and mass spectrometry. The term "exposure" is used in it's ordinary sense and includes exposing cells to a compound by placing the compound in their environment, e.g., in the medium, and includes exposing animals to a compound by injection, inhalation, consumption, external or internal application, supository and other means known in the art.

BRIEF DESCRIPTION OF THE DRAWINGS

FIGS. 2A–2I. Abnormal segmentation of axial skeleton, sclerotome and dorsal root ganglia (DRG) in PS1−/− embryos. 2A, E17.5 embryos were fixed and photographed intact; note the overall size reduction and the stubby tail of PS1−/− embryos as compared to a littermate control. 2B, 2C, Skeletal preparations of alizarin red (bone) and alcian blue (cartilage) stained PS1−/− (2B) and PS1+/+ (2C) E17.5 embryo. Note the vertebral rudiments are fused in PS1−/− embryo (2B) whereas the vertebral column in littermate control (2C) is orderly segmented. 2D, 2E, Saggital section of E15.5 PS1−/− embryo (2D) shows abnormal segmentation of vertebral column (arrow) adjacent to spinal cord (denoted by *) and fusion of dorsal arches (arrowhead) as compared to PS1+/− control (2E). 2F, 2G, Sclerotome of PS1−/− (2F) and PS1+/− (2G) embryos at E11.5. The arrow in panel g points to the condensation of sclerotomic material in PS1+/− embryo whereas the intrasegmental condensation (arrow in panel 2F) has not yet occurred in the PS1−/− embryo. The asterisks denote spinal cord. 2H, 2I, Parasaggittal section of E15.5 PS1−/− embryo (2H) showing fusion of DRG denoted by an asterisk; arrow points to nonsegmented axial skeleton. DRGs, indicated by an asterisk, are segmented in E15.5 PS1+/− embryo (2i). Sections in 2D and 2E were stained with Masson trichrome and sections in 2F–2I were stained with hematoxylin and eosin.

Bars: 2F, 2G=200 mm; 2H, 2I=100 mm.

FIGS. 3A–3F. Abnormal segmentation of somites in PS1−/− embryos. 3A, 3B, PS1+/− (3A) and PS1−/− (3B) E9.5 embryos were fixed and photographed intact. 3C, 3D, Higher magnification of PS1+/− and PS1−/− embryos. An ordered array of somites is apparent in PS1+/− embryos (3C) while some somites in PS1−/− embryos (3D) appear compressed (arrowheads), and fused (*); note the unsegmented condensation of somites (bracketed in 3D). 3E, 3F, Somite segmentation in wild-type (not shown) or PS1+/− (3E) embryos is coordinated across the midline whereas asymmetric segmentation of somites is observed in PS1−/− embryo (3F). Sections were stained with hematoxylin and eosin.

Bar=100 mm.

FIGS. 4A–4G. Reduced expression of Notch 1 and Dll 1 in PS1−/− embryos. 4A–4D., Detection of Notch 1 mRNA by whole-mount in situ hybridization of E8.5 (4A, 4B) and E9.5 (4C, 4D) embryos. Note the reduction of Notch 1 signals in PS1−/− embryos in the presomitic mesoderm (indicated by brackets). 4E, 4F, Detection of Dll 1 mRNA by whole-mount in situ hybridization of E9.5 embryos. Note the decreased Dll 1 signal in PS1−/− embryo in the presomitic mesoderm (indicated by bracket). 4G, Detection of PS1 MRNA by whole-mount in situ hybridization of E9.5 embryos. Arrows point to the somites and bracket denotes the presomitic mesoderm. Control, (4A, 4C, 4E, 4G); PS1−/−, (4B, 4D, 4F).

FIGS. 5A–5F. Central nervous system (CNS) hemorrhage and skull base deformities in PS1−/− embryos. 5A, Marked brain hemorrhage is evident in PS1−/− (upper left [side view] and lower left [top view]) compared to PS1+/− (upper right [side view] and lower right [top view]) intact E15.5 embryo. 5B, Hemorrhage occurs within ventricles (indicated by an asterisk), connective tissue overlying the brain (primitive leptomeninges; arrowhead) and parenchyma (arrow). 5C, and 5E, Mid-sagittal sections of E15.5 PS1−/− embryo (5C) shows CNS hemorrhage and skeletal deformities not seen in a PS1+/− littermate (5E). Note the severe bending of the basioccipital bone and the downward disposition of the hindbrain and brainstem. 5D and 5F, Higher magnification of regions boxed in 5C and 5E, respectively, showing the distorted angle (arrowhead) formed between the basioccipital bone (arrow) and the atlas in the PS1−/− (5D) as compared to mPS1+/− (5F) embryo. The posterior pharynx at the esophageal opening is marked by an asterisks for orientation. Sections in 5B–5F were stained with Masson trichrome.

Bar for 5B, 5D and 5F=200 mm; 5C and 5E=300 mm.

Figure 6A:
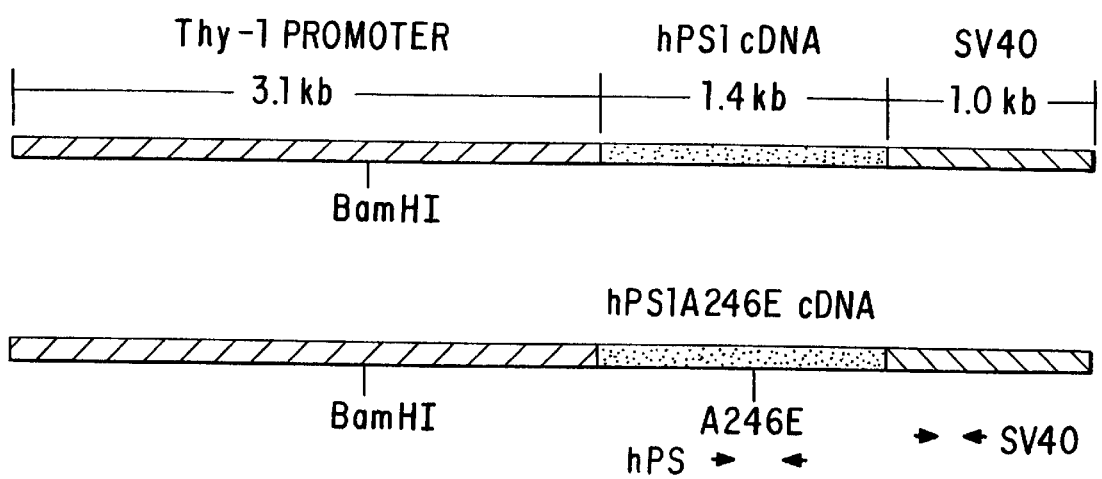
Figure 6B:
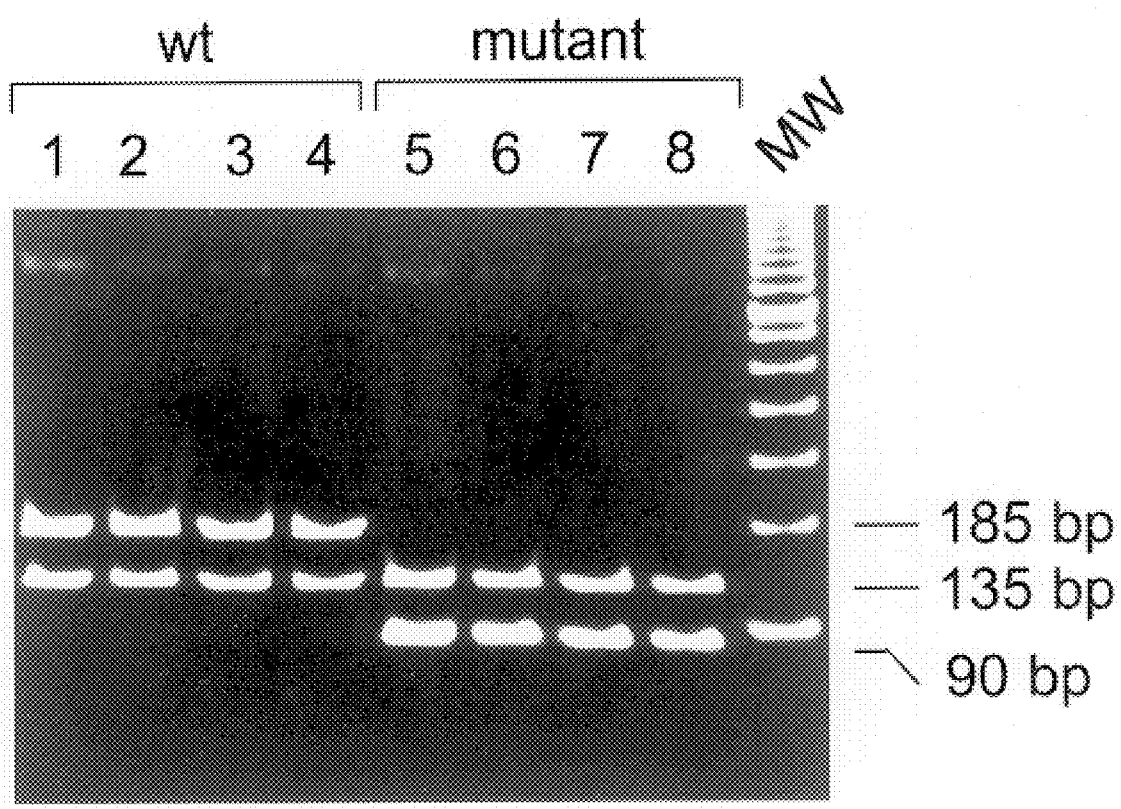

FIGS. 6A–6B. (6A) Schematic representation of the wild type and mutant human PS1 (hPS1 and hPS1A246E, respectively) transgene constructs. The 1.4 kb PS1 and PS1-1A246E cDNAs were inserted between the human Thy-1 promoter and SV40 splicing/polyadenlynation sequence. Two PCR primer pairs were drawn below the map. The SV40 primer pair amplifies a 300 bp fragment for transgene genotyping. The hPS1 primer pair covering the A246E site was designed to verify the mutation site in transgenic mice. (6B) PCR typing of wild type and mutant transgenes in transgenic mice from four Thy-PS1 lines (lane 1–4) and four Thy-PS1A246E lines (lane 5–8). A 320 bp PCR fragment encompassing the mutation site was amplified from tail DNAs using the hPS1 primer pair and digested with DdeI. Two fragments of 185 bp and 135 bp were generated from wild type PS1 transgenic mice. A246E mutation creates a new DdeI site in the 185 bp fragment, which was converted by DdeI digestion into two 95 bp fragments, as shown in lane 5–8.

Figure 7A:
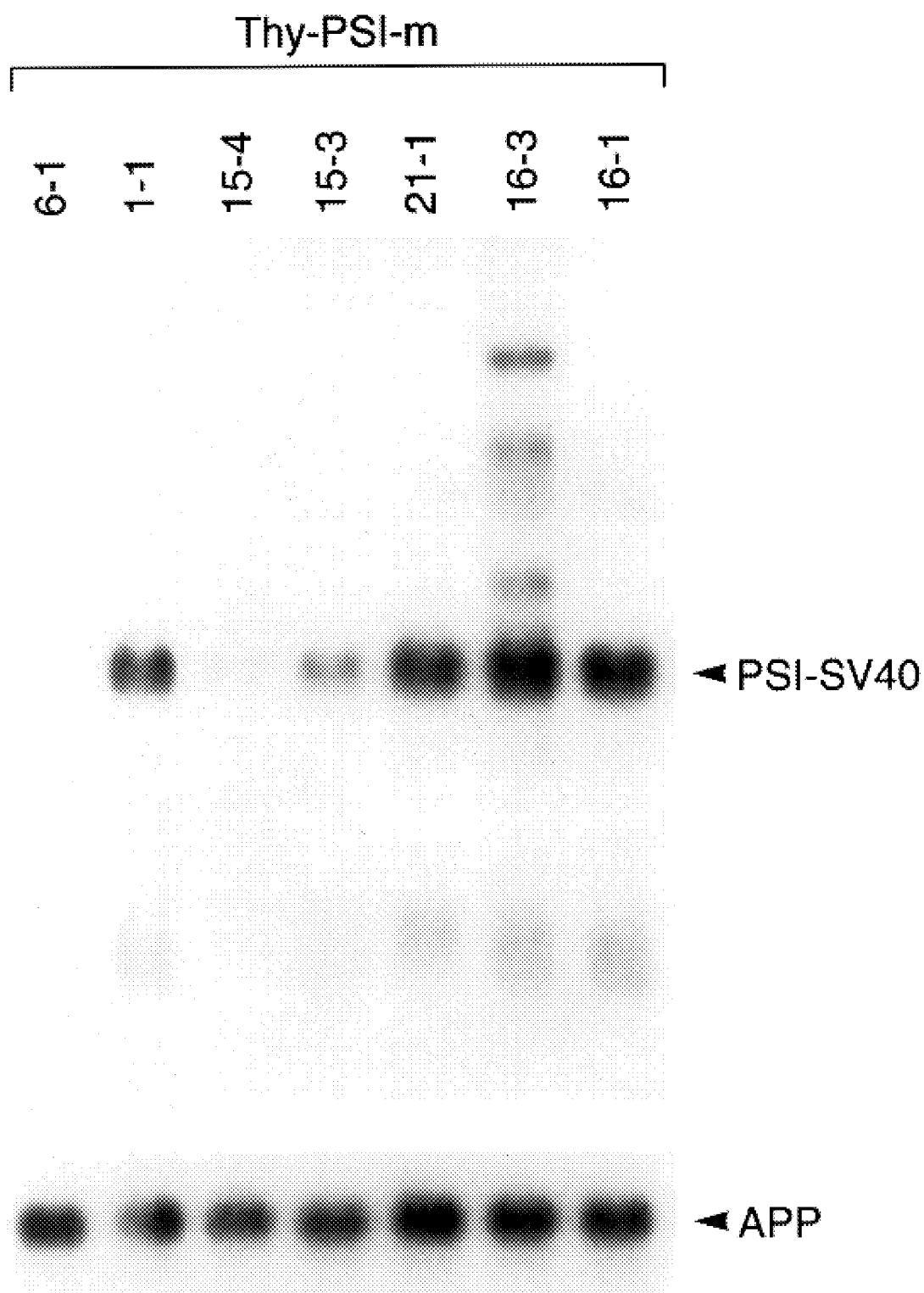
Figure 7B:
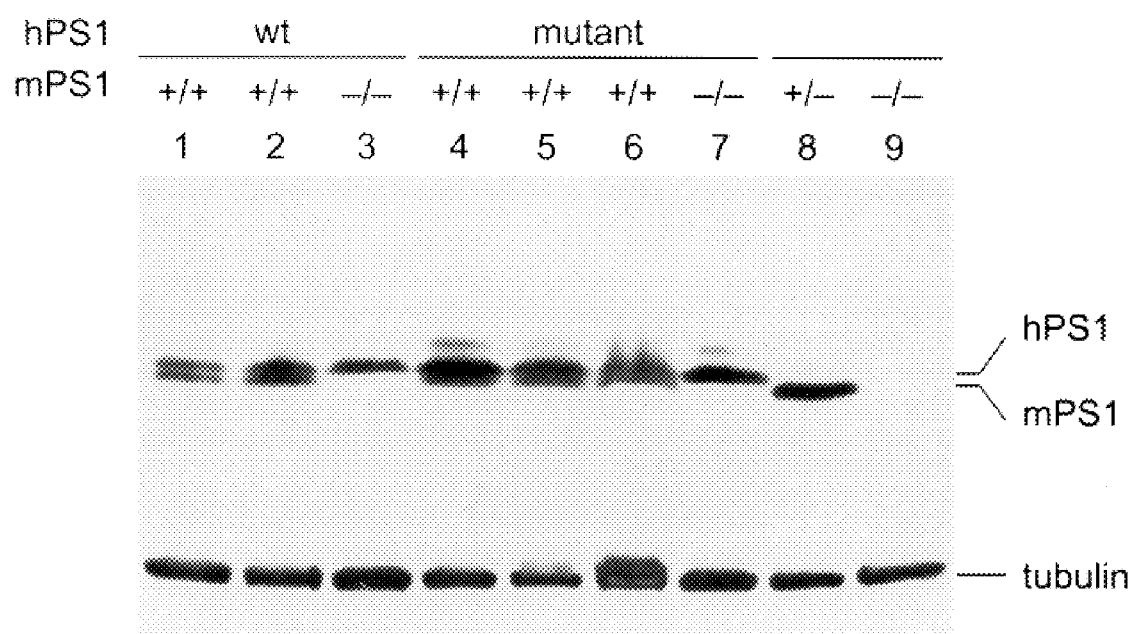

FIGS. 7A–7B. 7A shows a northern analysis of transgene expression. 15 mg/lane total brain RNA was resolved by a denaturing formaldehyde gel, transferred to a nylon membrane and hybridized with a transgene specific SV40 probe. The bottom panel shows an APP loading control. 7B. Immunoblot of brain (lanes 1–7) and embryonic (lanes 8–9) protein lysate (60 mg) reacted with the PS1 loop antibody, demonstrating the expression of human PS1 protein in transgenic and escued lines. Lane 1, 2—two Thy-PS1 transgenic lines showing about equal signal intensity for hPS1 (upper band) and mPS1 (lower band). Lane 3—a Thy-PS1 rescue line expressing hPS1 only. Lane 4–6—three Thy-PS1A246E transgenic lines expressing both the hPS1 and mPS1. Note that transgenic lines represented by lane 4 and 5 expressed more hPS1 than native MPS1. Lane 7—a Thy-PS1A246E rescue line expressing only hPS1. Lane 8 and 9—day 18.5 embryonic protein extract from a heterozygous (+/−) and a homozygous (−/−) PS1 knockout mouse, respectively. Bottom panel is a β-tubulin loading control.

Figure 8:
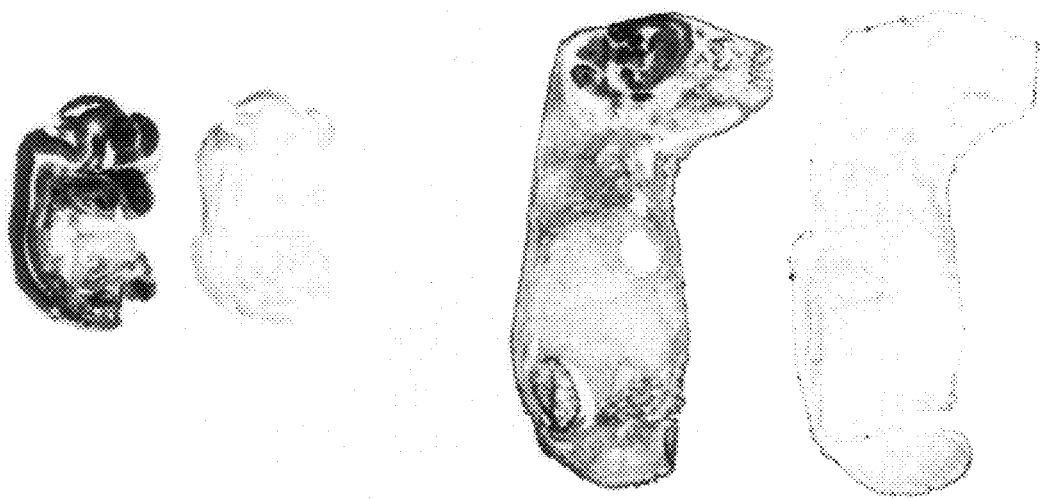
Figure 8:
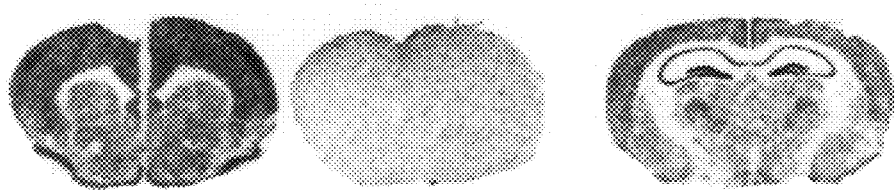
Figure 8:
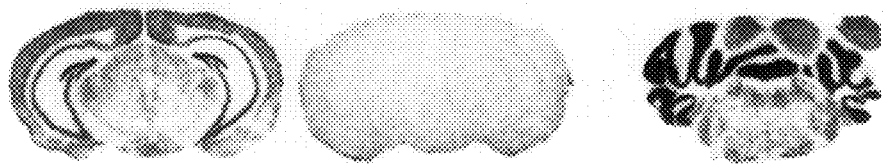

FIG. 8. In situ hybridization analysis of developmental and tissue specific expression of the human PS1 transgene, using a transgene specific SV40 oligo probe. Ubiquitous expression in various adult brain areas, and in embryonic tissues (E13.5 and E18.5) were detected on sections from a Thy-PS1A246E transgenic line 16-3. The transgenic mRNA was most abundant in hippcampus and cerebellum in adult brain. On sagittal sections of E13.5 embryo, strong hybridization signal is found along vertebral column and spinal cord, tissues most affected in PS1 null embryos. The tissue distribution of human PS1 mRNA became restricted to CNS in E18.5 embryos. On each panel, the left figure represents the hybridization image and the figure shown on the right is a control section hybridization in the presence of 100×fold cold probe.

FIGS. 9A—9D. Newborn skeletal preparations stained with alizarin red and alcian blue. Comparing with wild type (9A) and PS1 null (9B) samples, Thy-PS1A246E rescued mouse (9D, line 16-3) showed almost complete correction of vertebrate defects except the minor kink seen in tail. It has normal number of 7 cervical, and 13 thoracic vertebrae, as seen in (9A), in comparison to the varying 4-6 cervical, 9-10 thoracic segments found in knockout mouse. The ossification centers are well developed and properly organized as in the wild type skeleton. Thy-PS1 rescued mouse (9C, line 10-8) showed vast improvement in cervical and thoracic regions over the knockout mouse (9B). But it still has missing ribs and its lumbar-tail segments are disorganized and showed delayed and unsymmetric ossification, resulting in a split vertebrate and twist tail.

DETAILED DESCRIPTION OF THE INVENTION

The present invention relates to a transgenic non-human animal lacking native PS1 protein (PS1 null) and to the animal having a non-native PS1 protein expressed either in the presence or absence of the native PS1. The transgenic animal of the invention can be used in the study of the expression and activity of the PS1 gene and protein, the effect of FAD mutations on the expression and activity of PS1, modulators of the activity of the PS1 gene or protein, and aspects of disorders involving the central nervous system, e.g., Alzheimer's Disease.

The generation of PS1 deficient transgenic non-human animals, including mice, aids in defining the in vivo function (s) of PS1. Such PS1 null animals can be used as a strain for the insertion of human PS1 genes, and provides an animal model useful in the design and assessment of various approaches to modulating PS1 activity and expression. Such modified transgenic non-human animals can also be used as a source of cells for cell culture. These cells can be used for corresponding in vitro studies of PS1 expression, activity and the modulation thereof.

The murine PS1 gene is about 75 kb in size and is encoded by 10 exons. The human PS1 cDNA is about 1.4 kb. An animal without an activate PS1 gene could be used to evaluate the role of PS1 in animal development and in the central nervous system. However, it was not known if such an animal could be produced, e.g., if such an animal be viable. Herein, the production of both PS1 knock-out mice exhibiting a null-lethal phenotype and transgenic mice expressing human wild-type or FAD mutant PS1 in a murine knock-out background is described. Mice heterozygous for an inactivated native PS1 allele and mice carrying a human PS1 gene were intercrossed to generate transgenic mice of which the only PS1 expressed is that of human origin. Both the wild-type and a representative FAD mutant form of the human gene are used. These animals are useful as an animal model for studying aspects of FAD.

The present invention utilizes a nucleic acid molecule encoding a portion of a PS1 gene or a complete coding sequence. Transgenic animals are generated which have an altered PS1 gene. A PS1 gene that naturally occurs in the animal is referred to as the native gene, and if it is not mutant, it can also be referred to as wild-type. The alterations to an native gene include modifications, deletions and substitutions. Modifications, deletions and substitutions can render the native gene nonfunctional, producing a "knockout" animal, or can lead to a PS1 with altered expression or activity. These transgenic animals are useful for drug antagonist or agonist studies, for animal models of human diseases, and for testing of treatment of disorders or diseases associated with PS1. Transgenic animals lacking native PS1 are useful in characterizing the in vivo function(s) of PS1. A transgenic animal carrying a non-native PS1 in the absence of native PS1 is useful for the establishment of a non-human model for diseases involving PS1, for studies of non-native PS1, to study modulators of the non-native gene and to distinguish between the activities of the non-native PS1 in in vivo and in vitro systems.

Surprisingly, a null-lethal knockout animal of this invention is viable when a human PS1 transgene is present, regardless of whether the non-native gene is a wild-type or mutant allele. Thus, the knockout animal can be rescued and used in the study of a variety of PS1 genes or a variety of modifications of a particular PS1 gene in the H absence of any background effects from the PS1 gene native to the transgenic animal.

The term "animal" is used herein to include all mammals, except that when referring to transgenic animals, the use of the term excludes humans. It also includes an individual animal in all stages of development, including embryonic and fetal stages. A "transgenic animal" is an animal containing one or more cells bearing genetic information received, directly or indirectly, by deliberate genetic manipulation at a subcellular level, such as by microinjection or infection with recombinant virus. This introduced DNA molecule can be integrated within a chromosome, or it can be extra-chromosomally replicating DNA. Unless otherwise noted or understood from the context of the description of an animal, the term "transgenic animal" as used herein refers to a transgenic animal in which the genetic information was introduced into a germ line cell, thereby conferring the ability to transfer the information to offspring. If offspring in fact possess some or all of the genetic information, then they, too, are transgenic animals. The genetic information is typically provided in the form of a transgene carried by the transgenic animal.

The genetic information received by the animal can be foreign to the species of animal to which the recipient belongs, or foreign only to the particular individual recipient. In the last case, the information can be altered or it can be expressed differently than the native gene. Alternatively, the altered or introduced gene can cause the native gene to become non-functional to produce a "knockout" animal.

As used herein, a "targeted gene" or "Knockout" (KO) is a DNA sequence introduced into the germline of a nonhuman animal by way of human intervention, including but not limited to, the methods described herein. The targeted genes of the invention include nucleic acid sequences which are designed to specifically alter cognate endogenous alleles.

An altered PS1 gene should not fully encode the same PS1 as native to the host animal, and its expression product can be altered to a minor or great degree, or absent altogether. In cases where it is useful to express a non-native PS1 gene in a transgenic animal in the absence of a native PS1 gene we prefer that the altered PS1 gene induce a null lethal knockout phenotype in the animal. However a more modestly modified PS1 gene can also be useful and is within the scope of the present invention.

A type of target cell for transgene introduction is the embryonic stem cell (ES). ES cells can be obtained from pre-implantation embryos cultured in vitro and fused with embryos (M. J. Evans et al, Nature 292:154–156 (1981); Bradley et al., Nature 309:255–258 (1984); Gossler et al. Proc. Natl. Acad. Sci. USA 83:9065–9069 (1986); and Robertson et al., Nature 322:445–448 (1986)). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (R. Jaenisch, Science 240: 1468–1474 (1988)).

The functions of PS1 are believed to be complex, but they can be examined in a variety of ways. One approach to the problem of determining the contributions of individual genes and their expression products is to use isolated genes to selectively inactivate the native wild-type gene in totipotent ES cells (such as those described herein) and then generate transgenic mice. Techniques are available to inactivate or alter any genetic region to any mutation desired by using targeted homologous recombination to insert specific changes into chromosomal alleles. The use of gene-targeted ES cells in the generation of gene-targeted transgenic mice was described in 1987 (Thomas et al., Cell 51:503–512, (1987)) and is reviewed elsewhere (Frohman et al., Cell 56:145–147. (1989); Capeccbi, Trends in Genet. 5:70–76 (1989); Baribault et al., Mol. Biol. Med. 6:481–492, (1989); Wagner, EMBO J. 9:3025–3032 (1990); Bradley et al., BioTechnology 10:534–539 (1992)).

The methods for evaluating the targeted recombination events as well as the resulting knockout mice are readily available and known in the art. Such methods include, but are not limited to DNA (Southern) hybridization to detect the targeted allele, polymerase chain reaction (PCR), polyacrylamide gel electrophoresis (PAGE) and Western blots to detect DNA, RNA and protein.

The following examples are presented by the way of illustration and, because various other embodiments will be apparent to those in the art, the following is not to be construed as a limitation on the scope of the invention.

EXAMPLE 1

Construction of Murine Presenilin 1 Gene Targeting Vector

Genomic clones containing exon 4 of mouse PS1 gene were isolated from a 129Sv strain of mouse (Lambda FIX II library, Stratagene, La Jolla, Calif.). From the knowledge of the genomic organization of mouse PS1 gene with regard to restriction sites and the fourth exon, a gene targeting vector for inactivating the PS1 gene was prepared using standard cloning techniques (Sambrook et al., Molecular Cloning,A Laboratory Manual, Cold Spring Harbor Laboratory Press, 1989).

Figure 1A:
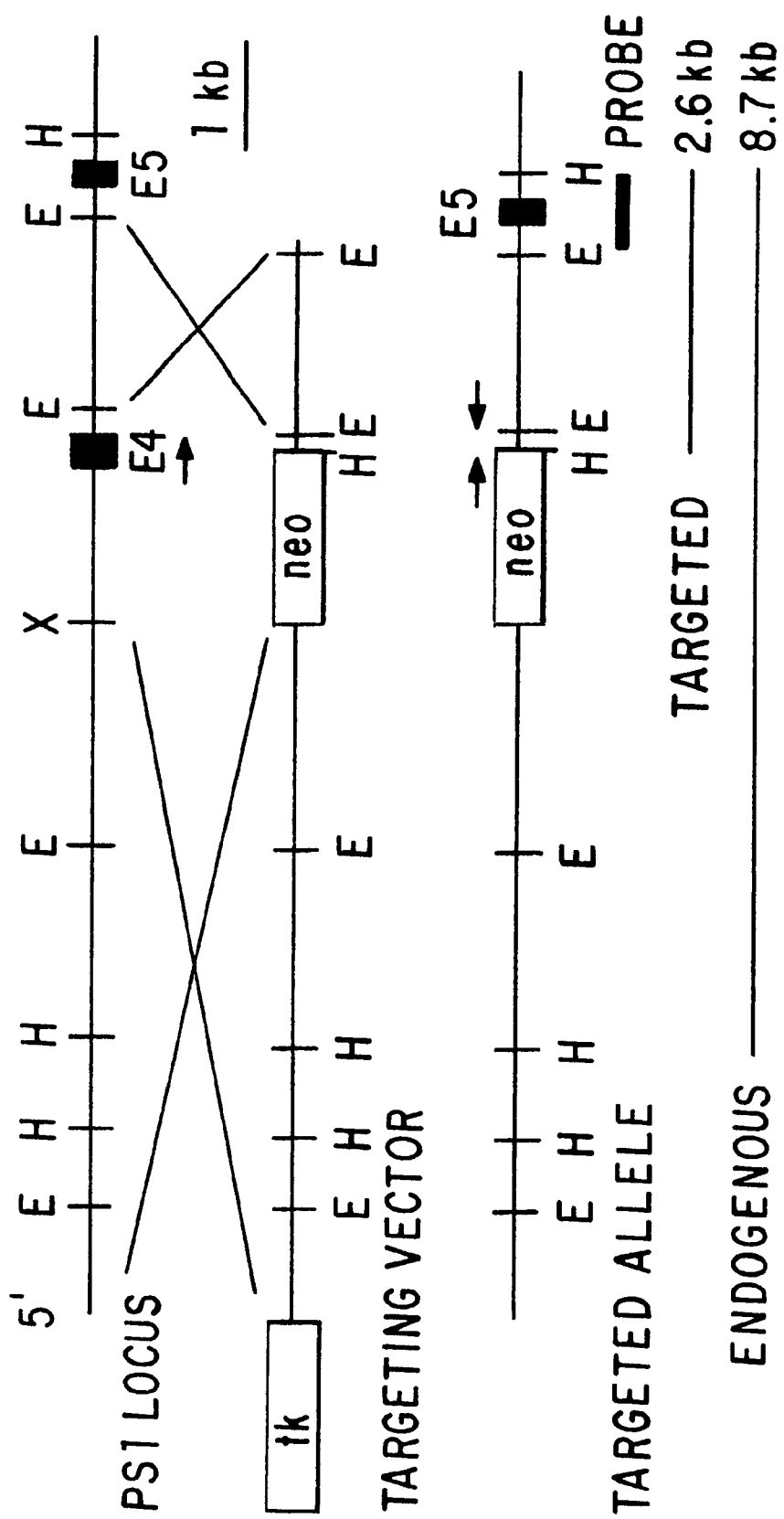
FIGS. 1A–1D. 1A is a schematic representation of a genomic map of a portion of the mouse PS1 gene including exon 4 (E4) and the disruption of the mouse chromosomal PS1 gene by targeted recombination using replacement vector pPS1KO. R: EcoRI, H: HindIII. 1B shows a Southern hybridization analysis of wild-type and two targeted embryonic stem (ES) clones (lanes a, b, and c respectively) and embryos either homozygous (−/−), wild-type (+/+) or heterozygous (+/−) for the disrupted PS1 alleles (lanes d, e, and f), as a result of heterozygous matings. iC is the PCR analysis of DNA extracted from yoke sac of embryos. Using primers indicated in panel A, the 370-bp (by neo sense primer and PS1 antisense primer) or 500-bp (by PS1 sense primer and PS1 antisense primer) fragment is specific to the targeted or endogenous PS1 allele respectively. The sequences of the primers are: neo sense: 5'-CCATTGCTCAGCGGTGCTG-3' (SEQ ID NO: 1); PS1 sense: 5'-CTGCTGCAGGTGGCTCTGCA-3' (SEQ ID NO: 2); PS1 antisense: 5'-CAGCTCTATACAAGCAAACAAG-3' (SEQ ID NO: 3). 1D shows an immunoblot of total protein extracts (100 mg) of wild-type (+/+), heterozygous (+/−) and homozygous (−/−) PS1 knockout embryos at embryonic day 18.5 (E18.5).
Figure 1B:
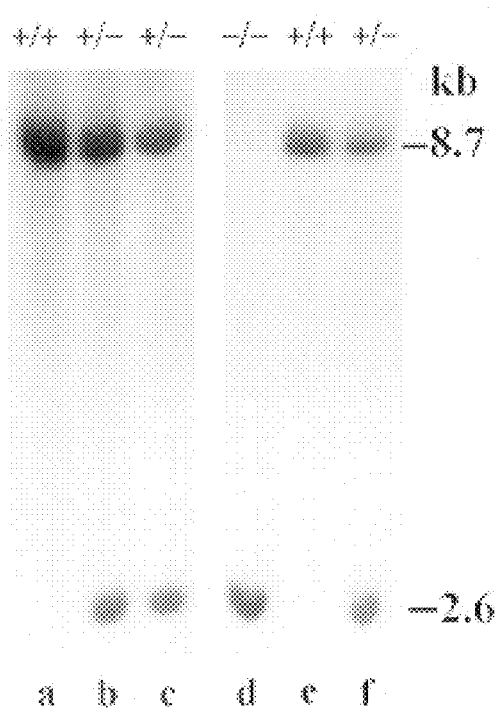

Referring to FIG. 1A, the targeting vector (pPS1KO (ATCC 98433 Deposited May 14, 1997)) contains from left to right: 6.0 kb of 5' homology with the PS1 locus; a PGKneo expression cassette inserted in the opposite orientation to the PS1 gene; a fragment of 1.7 kb homologous to the 3' part of the PS1 gene; A MC1-TK gene was cloned upstream of the 5' homologous sequence for negative selection (Mansour et al. 336, 348–352, (1988)). Targeted recombination between the vector and the wild-type PS1 locus results in the deletion of a 1.9 kb of the PS1 gene including exon 4 followed by its replacement with the neomycin resistance gene.

EXAMPLE 2

Targeted Disruption of the PS1 Gene in Murine ES Cells

The pPS1KO targeting vector of Example 1 was used in PS1 gene disruption experiments. The vector was linearized at a unique BamHI site before electroporating into AB2.1 ES cells. The AB2.1 ES cells were cultured on SNL feeder cells (Robertson, in Teratocarcinomas and embryonic stem cells, IRL Press, pp. 71–112 (1987)) and the selection of targeted PS1 clones (Zheng et al., Cell 81:525–531 (1995)) were performed by techniques known in the art. ES cell DNA (8 μg) from the wild-type AB2.1 cells and the clones were digested with restriction enzyme HindIII, electrophoresed on a 0.7% agarose gel, transferred onto a Gene Screen Plus nylon membrane (NEN-Dupont). The hybridization probe used for Southern blot analysis were a 0.7 kb EcoRI-HindIII fragment downstream of the 3' homologous sequence (FIG. 1A). HindIII digestion, which generates a 8.7 kb wild-type allele and a 2.6 kb targeted allele, was used to differentiate the alleles. The 2.6 kb diagnostic fragment is detected by the probe in the targeted clones in addition to the wild-type 8.7 kb fragment.

A total of 55 targeted clones were identified from a total of 700 clones analyzed. Six clones were used for further experiments.

EXAMPLE 3

Production of Chimeric Mice

Six PS1 targeted ES clones were injected into C57BL/6J recipient blastocysts in separate experiments using routine techniques (Bradley, A. "Production and analysis of chimeric mice. In Teratocarcinomas and Embryonic Stem Cells: A Practical Approach", E. J. Robertson, ed. Oxford:IRL Press, (1987), ppll3–151). As the ES cell line AB2.1 is homozygous for the agouti (A) coat color gene, penetrance of ES cells into the injected (black coat color) C57Bl/6 blastocyst gives rise to chimeric coat color mice. Among the six ES clones, clone #300 yielded 7 male chimeras and no female chimeras, with the chimerism ranging from 90% to 100%. Clone #688 yielded 3 male chimeras and 1 female chimera with chimerism ranging from 50% to 100%.

EXAMPLE 4

Generation of Heterozygous PS1 Knockout Mice and Homozygous PS1 Knockout Embryos The chimeric mice were bred to wild-type C57BL16 female mice. Germline transmission was achieved with both clone #300 and clone #688 as evidenced by the appearance of agouti offspring. To determine the. PS1 genotypes, genomic DNA was purified from about 1 cm of tail taken from each mouse. Southern hybridization analysis, described above, was used to confirm offspring which contained the disrupted PS1 allele. ES cell DNA from the wild-type AB2.1 cells and clones #300 and #688 were used as controls.

These transgenic offspring were heterozygous for the PS1 disruption. Male and female transgenic mice, each of which contained one copy of the altered murine PS1 allele (heterozygous mice, or PS1 +/−), were mated with each other to generate mice in which both copies of the PS1 gene encoded the targeted, altered PS1 allele (homozygous mice, or PS1−/−). It was predicted that one fourth of the mice would be homozygous for the altered PS1 gene, provided such mice were viable. Mice from over sixty litters were assessed for homozygosity. None were identified, demonstrating the PS1−/− mice have a null lethal phenotype. When over sixty litters of mouse embryos were assessed, it was determined that mouse embryos homozygous PS1−/− were present at expected Mendelian frequencies at various stages of gestation ranging from E8.5 to E18.5.

EXAMPLE 5

Confirmation of PS1 Inactivation by Western Blot Analysis

Figure 1C:
Figure 1D:
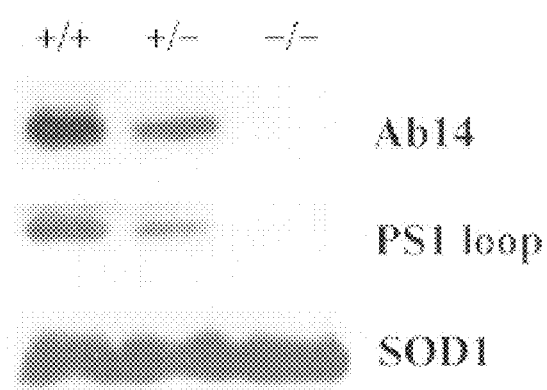

Immunoblot of total protein extracts (100 mg) of wild-type (+/+), heterozygous (+/−) and homozygous (−/−) PS1 knockout embryos at embryonic day 18.5 (E18.5) was performed (FIG. 1C). The antibodies used are rabbit polyclonal antisera specific for epitopes in the N-terminus (AB 14) and the "loop" region (PS1 loop). Superoxide dismutase 1(SOD1) is used as an internal standard.

In PS1+/− mice, PS1 derivatives accumulate to approximately 50% of the level of control littermates. Homozygous PS1 knockout (PS1−/−) embryos showed no evidence of accumulation of PS1 related polypeptides, thus confirming a complete inactivation of the gene in the homozygous embryos.

EXAMPLE 6

Characterization of Homozygous PS1 Deficient Mice

From over sixty litters examined, no mouse homozygous PS1 −/− survived beyond day one after birth. However, PS1−/− embryos were present at expected Mendelian frequencies at various stages of gestation ranging from E8.5 to E18.5 (>60 litters examined). To date, we have not observed any developmental deficits in mice heterozygous for a mutant allele of PS1.

The most striking phenotype observed in PS1−/− embryos was a severe perturbation in the development of the axial skeleton. The PS1−/− mutant embryos (E10.5 to E18.5) are smaller compared to controls and possess a stubby tail (FIG. 2A). Histochemical analysis of the skeleton of PS1−/− E17.5 embryos using alizarin red and alcian blue stains revealed considerable defects in the differentiation of vertebral column (FIGS. 2B, 2C) and the ribs (not shown). The limbs appeared normal.

Embryos were prepared and sectioned as follows. Embryos were fixed in 4% paraformaldehyde for 2 hours at 27° C., dehydrated, embedded in paraffin and sectioned at 10 mm. Sections were stained with either hematoxylin and eosin or Masson trichrome for histological analysis. In midsaggital sections from E15.5 PS1−/− embryos, one observes that the vertebral column is drastically shortened and fails to undergo proper segmentation as compared to controls (FIGS. 2D, 2E). In addition, abnormalities of the basioccipital bone (skull plate) including deformities and malorientation in relation to the vertebral column were apparent (FIG. 2D). In contrast, control embryos show a normal skull plate which reside in a nearly perpendicular position with respect to the vertebral column (FIG. 2E). The finding that development of the axial skeleton is severely perturbed in PS1−/− animals indicated a defect in the differentiation of the sclerotome. Comparison of PS1−/− E11.5 embryos with controls disclosed that sclerotome condensation in PS1−/− embryos was markedly delayed (FIG. 2F) as compared to control littermates in which the ventromedial portion of the sclerotome differentiates and condenses and subsequently separates from the anterior region of the somitic segment (FIG. 2G). These data indicate that delayed sclerotome condensation leads to deficits in development of the vertebral column.

Figure 3A:
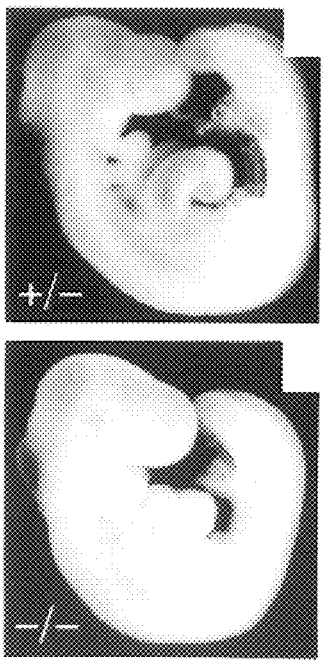
Figure 3C:
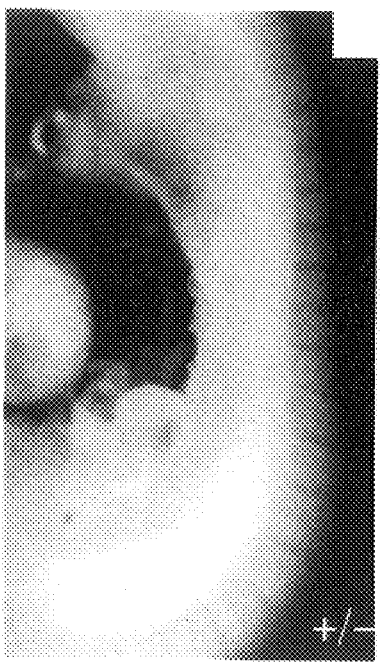
Figure 3D:
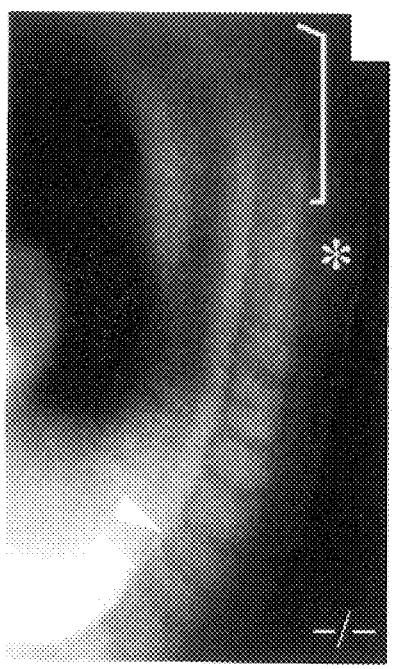
Figure 3E:
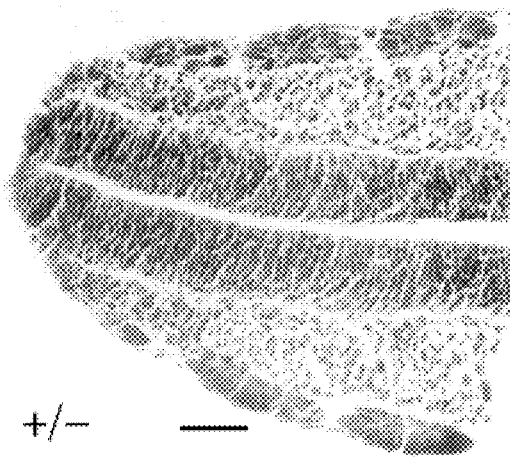
Figure 3F:
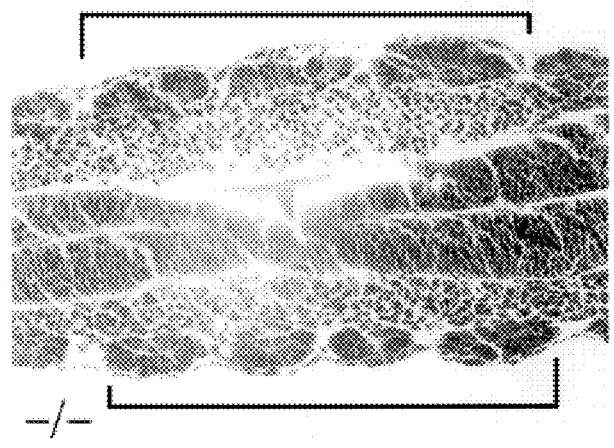

Interestingly, the dorsal root ganglia (DRGs) in PS1−/− embryos were fused over multiple segments along the cranio-caudal axis of the vertebral column (FIGS. 2H, 2I). Collectively, the delayed condensation of sclerotome and the fused DRGs in PS1−/− embryos indicated that these phenotypes might have arisen as a consequence of earlier deficits in somitogenesis. To determine whether somitogenesis is affected in PS1−/− embryos, embryos were examined between E8.5 and E10.5, a time interval during which somites are being generated. From intact E9.5 PS1−/− embryos, observed irregularly shaped somites are observed along the entire length of the neural tube; somites were largely absent at the caudal-most regions (FIGS. 3B and 3D). Further histological examination of E9.5 PS1 −/− embryos revealed misalignment of somites (FIG. 3F) compared to wild type embryos in which somites are in tight register across the midline (FIG. 3E).

Figure 4A:
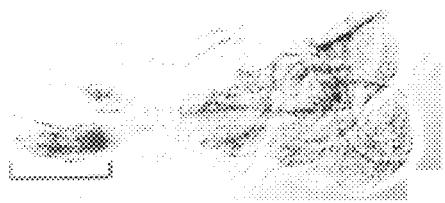
Figure 4B:
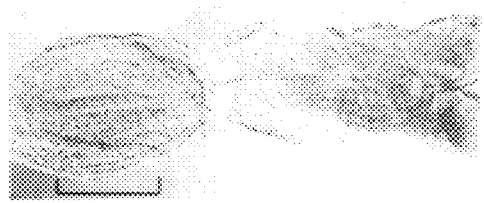
Figure 4C:
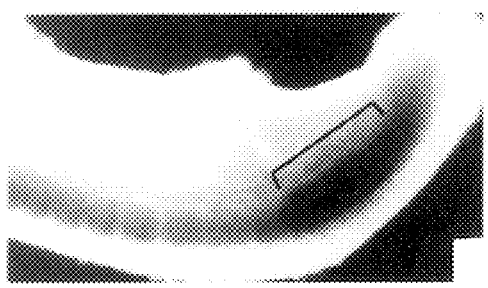
Figure 4D:
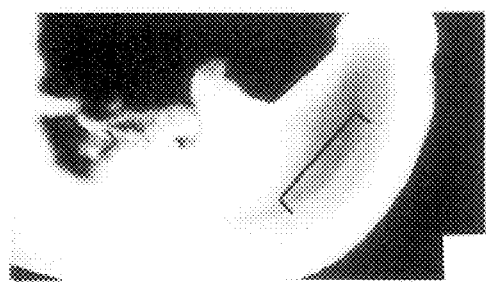
Figure 4E:
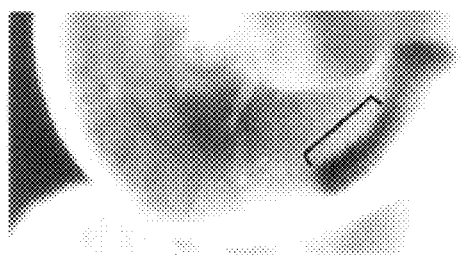
Figure 4F:
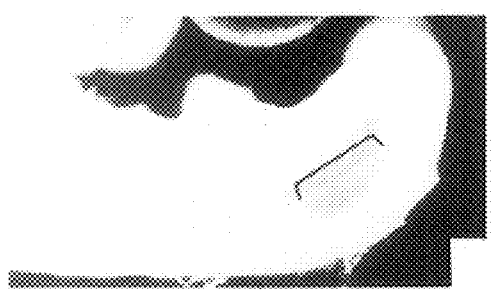
Figure 4G:

In view of the similarities in somite segmentation defects in PS1−/− embryos and embryos with functionally inactivated Notch 1 (Conlon, RA., et al. Development, 121:1533–1545 (1995)) or Dll 1 (Hrabe de Angelis, M., et al., Nature, 386:717–721 (1997)) alleles, we examined the expression of Notch 1 and Dll 1 mRNA in PS1 −/− embryos. At E8.5 and E9.5 embryos, the abundant expression of Notch 1 mRNA observed in the presomitic mesoderm of control embryos (FIGS. 4A and 4C, respectively) is nearly abolished in the PS1−/− embryos (FIGS. 4B and 4D, respectively). Analysis of Dll 1 mRNA expression revealed that while high levels of Dll 1 mRNAs are observed in the presomitic mesoderm of E9.5 control embryos (FIG. 4E), the levels are markedly reduced in PS1−/− embryos (FIG. 4F). In addition, it was confirmed that PS1 mRNAs are also expressed in the presomitic mesoderm and somites in wild-type embryos (FIG. 4G), albeit at significantly lower levels compared to Notch 1 and Dll.

These data, indicate that PS1 serves to regulate the spatiotemporal expression of Notch 1 and Dll 1 in the paraxial mesoderm. The particular mechanisms by which PS1 influences extrinsic or intrinsic signaling pathways necessary for cell-autonomous amplification of Notch 1 or Dll 1 mRNA in the presomitic mesoderm remains to be established.

Figure 5A:
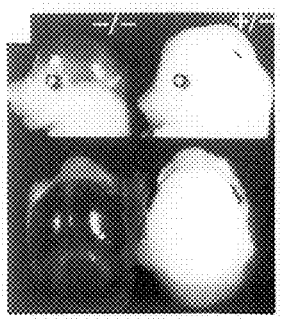
Figure 5C:
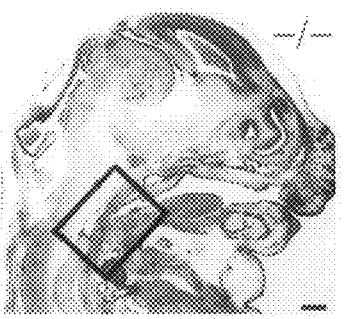
Figure 5E:
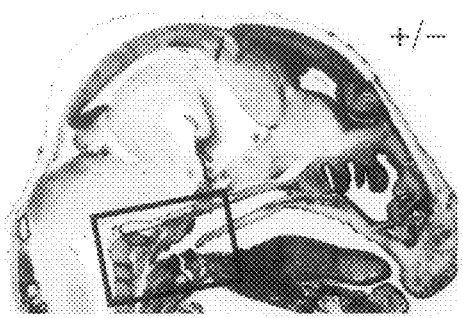
Figure 5B:
Figure 5D:
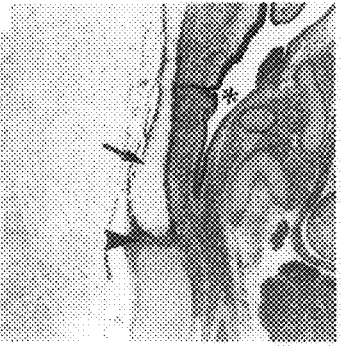
Figure 5F:
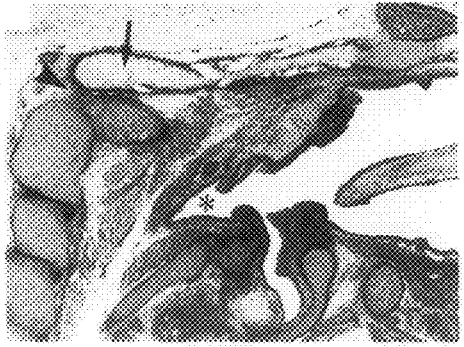

Although the cellularity and cytoarchitecture of the developing brain of PS1−/− embryos appeared normal, all PS1−/− embryos after E11.5 exhibited hemorrhages limited to the brain (FIG. 5A) and/or spinal cord; these lesions were not seen in PS1+/− or PS1+/+ littermates. The severity of the hemorrhages varied between individual embryos. To determine the origin of hemorrhages, we histologically examined PS1−/− embryos at E13.5 and established that the hemorrhages are present beneath the primordial dura and leptomeninges, within the ventricles and in neural parenchyma (FIG. 5B).

EXAMPLE 7

Construction of Human PS1 Expression Vectors Using the Neuronal Specific Human Thy-1 Promoter Expression vectors Thy-PS1 (ATCC 209034 Deposited May 15, 1997) and Thy-PS1A246E (ATCC 209035 Deposited May 15, 1997), having PS1 alleles under the control of neuronal specific human Thy-1, promoter were generated by ligating a 1.8 kb KpnI-Bam HI digested fragment containing PS1 (or PS1A246E) cDNA sequences with KpnI-BglII cleaved pHZ024 vector. The directionality of the inserted gene was confirmed by restriction digestions. In addition, the constructs were partially sequenced to confirm the mutation.

Detailed Construction of plasmid pHZ024 is as follows:

a. pBSHT1 contains a 8 kb EcoRI fragment of human Thy-1 gene (hThy-1) in pBSV (gift of Dr. F. Grosveld, MRC, Mill Hill, London, UK; Van Rijs et al. Proc. Natl. Acad. Sci. USA 82: 5832–5835, 1985)

b. The 3.7 kb E.coRI-BglII fragment of pBSHT1 containing the hThy-1 promoter and the ATG translation initiation codon was cloned into EcoRI and BamHI site of pTZ18u, the resulting plasmid called pHZ020.

c. The 1.6 kb BamHI-BglII fragment containing the ATG initiation codon was cloned into the BanmHI site of pTZ18u (pHZ021a). A PCR amplification was carried out using pHZ021a as template and oligonucleotides T7 (in pTZ18u backbone) and oHZ002 (at the ATG initiation codon) as primers to generate a 1.3 kb product. The sequences of the primers are . . .

containing the ATG codon. The 1.3 kb PCR product was digested with NcoI-XbaI and inserted into the NcoI-XbaI digested pHZ020 (pHZ022).

e. A BglII linker was inserted at the SmaI site upstream of SV40 small T intron of pSV2neo (pHZ023). (Southern, P. J. & Berg,P. J. Mol. Appl. Genet. 1:327, 1982.) BglII linker: d(CAGATCTG)

f. The 1.0 kb SV40 small T intron & polyA was isolated by BglII & BamHI digestion of pHZ023 and ligated into the BglII digested pHZ022. The resulting plasmid, pHZ024, has the following features:

1. The vector contains two regulatory elements: the human Thy-1 promoter for brain-specific expression and the SV40 small T intron and polyA sequence for proper expression of the transgene.

2. The ATG initiation codon of the hThy-1 gene was mutated.

3. A polylinker cloning site was introduced downstream of hThy-1 promoter for insertion of genes to be expressed in transgenic mice.

EXAMPLE 8

Generation of Transgenic Mice Expressing Human PS1 Proteins Regulated by the Human Thy-1 Promoter A 5.8 kb Eco RI-Xba I fragment containing human Thy-1 promoter, PS1 (or PS1A246E) cDNA and SV 40 sequence was excised from the expression plasmid described above, gel purified and injected into the pronuclei of B6SJL/F1 embryos as described (Hogan, B. et al. Manipulating the Mouse Embryo, a Laboratory Manual. Cold Spring Harbor Laboratory, 1986). Founders identified by PCR and/or Southern hybridization were bred with B6SJL/F1 hybrid mice and transgenic progenies were identified by PCR. A transgene specific SV40 primer pair was used in PCR typing:

SV-sense: 5'-GTGAAGGAACCTTATTCTGTGGTG-3' (SEQ ID NO: 7);

SV-antisense: 5'-GTCCTTGGGGTCTTCTACCTTT CTC-3' (SEQ ID NO: 8) (Reneker et al., Development 121:1669–1680 (1995)). Transgenic lines expressing

```
T7: 5'-TAA TAC GAC TCA CTA TAG GG-3'(SEQ ID NO: 4)

SalI     XbaI     BglII    TaqI XhoI    ClaI    K-
pnI
OHZ002: 5'-ACG TCG ACT CTA GAA GAT CTT CGA CTC GAG ATC GAT GGT

SmaI            HindIII
ACC CGG GCA GGT TCA AGC TTC TGG GAT CTC AGT C-3'(SEQ ID NO: 5)
``` oHZ002 destroyed the ATG codon and introduced a polylinker cloning site in the PCR product, as schematically outlined below:

human PS1 were identified by Northern and Western blot analysis on brain lysate. Homozygous individuals were selected by Southern analysis on tail DNA.

5'-ACGTCGACTCTAGAAGATCTTCGACTCGAGATCGATGGTACCCGGGCAGGTTCAAGCTTCTGGGATCTCAGTC-3' (SEQ ID NO: 5)
                                                                    | |
                                              5'-TCATGGTTCTGGGATCTCAGTC-3' (SEQ ID NO: 6) Wild-type d. A NcoI partial digestion was performed on pHZ020 for cleavage at the downstream site only followed by a XbaI complete digestion to release the NcoI-XbaI fragment Transgene identities were identified in wild type and mutant transgenic lines by PCR typing. A hPS1 PCR primer pair encompassing the mutation site was designed to amplify a 320 bp fragment from mouse tail DNA using the following primers:

hPS1-sense: 5'-CTGGAAAGGTCCACTTCGACTC-3' (SEQ ID NO: 9);

hPS1-antisense: 5'-TGTGCTTTCTGCATTATACTTGG-3' (SEQ ID NO: 10).

The PCR product from Thy-PS1 transgene can be cleaved by restriction enzyme DdeI to generate a two band pattern of 185 bp and 135 bp. The same PCR product from Thy-PS1A246E transgene contains an additional DdeI site in the 185 bp sequence due to the A246E mutation. The mutation converts the 185 bp fragment into two 95 bp fragments upon DdeI digestion and generate a two band pattern of 135 bp and 95 bp. PCR genotyping on transgenic mice confirmed that the wild type and mutant transgenic lines all carried correct transgene (FIG. 6B).

EXAMPLE 9

Analysis of Transgenic Mice

A. Human PS1 RNA Expression by Northern Analysis

Northern analysis were used for initial assessment of transgene expression in different lines. Total brain RNA was isolated from individual transgenic lines using a Stratagene RNA purification kit. 15 mg RNA/lane was resolved on a 1.5% MOPS-fomaldehyde gene, transferred to GeneScreen Plus membrane, and hybridized by standard procedure using a SV40 splicing(polyadenylation probe or a human PS1 cDNAs probe. The amount of human PS1 mRNA in expressing lines ranged from 0.5× to 3× the level of endogenous mouse PS1 MRNA (FIG. 7A).

B. Human PS1 Protein Quantitation by Western Blot.

Western blot measurements on brain protein lysate using an anti-loop PS1 antibody (Thinakaran et al, Neuron 17:181–190 (1996)) detected proteolytically cleaved 19 kDa C-terminal fragment of both human and mouse PS1. Three Thy-PS1 lines and six Thy-PS1A246E lines expressing human PS1 protein were identified. Human PS1 levels in these lines range from about ¼ to 2× that of the endogenous mouse PS1 (FIG. 7B and Table 1). The protein expression level correlates well the mRNA level.

C. Human PS1 MRNA Distribution by In Situ Hybridization

In situ hybridization (Sirinathsinghji et al, in Molecular Imaging in Neuroscience, Sharif eds., pp 43–70, Oxford University Press, New York, (1993)) using a transgene specific SV40 oligo probe on brain sections revealed that the human PS1 mRNAs are expressed throughout brain, but are most abundant in bippocampus and cerebellum (FIG. 8).

We also examined the transgene expression pattern during embryogenesis on E9.5; 13.5; and 18.5 transgenic embryos. Weak and ubiquitous transgene expression was detected above control background in whole mount E9.5 embryos (not shown). The signal became stronger at E13.5, most obviously along vertebral column and spinal cord, areas most affected in null embryos (FIG. 8). At E18.5, transgene expression became restricted to CNS (FIG. 8).

EXAMPLE 10

Generation of PS1 Knockout Mouse Rescued by Human PS1 Transgenes

Human PS1 transgenic mice were mated with heterozygotes PS1 knockout mice. Double heterozygous F1s were selected by PCR typing and inter-crossed to produce progenies that are homozygous for the knockout allele in combination with one or two copies of the human transgenes.

Thy-1 promoter is reported to be active predominantly in neuronal and thymus tissues, substantially less so in other peripheral tissues, and is rather weak during pre-natal development (Kollias, PNAS 84:1492–1496 (1987), Gordon et al., Cell 50:445452 (1987)). The defective vertebrate and CNS hemorrhage phenotypes of PS1 null mouse, on the other hand, suggest that PS1 expression would be essential in somitogenic tissues, and possibly CNS vasculature, from early stages of embryogenesis. Our in situ hybridization data (FIG. 8) showed that Thy-1 promoter can be activated as early as embryonic day E9.5. Its activity is quite strong and widespread at E13.5 although the ubiquitous expression does become restricted to CNS at E18.5. Apparently, the dynamic Thy-1 promoter was able to provide critical PS1 activity required for normal development. Both the wild type and mutant Thy-PS1 transgenes rescued embryonic lethality of the PS1 null mouse and we were able to establish rescue lines expressing only human PS1 proteins.

EXAMPLE 11

Phenotypic Characterization of Humanized PS1 Transenic Mice

A. Wild Type Transgene Rescued Mice

Of two Thy-PS1 lines tested, line 10-8 partially rescued the null lethality. Rescued progenies heterozygous or homozygous for the transgene were viable and fertile. The rescue was partial because these mice still have some deformation of their vertebral skeletons and they tend to grow slower than wild type littermates. They are shorter in body length and have very short tails that are either severely twisted or hook-like in appearance. Low fertility rate was observed in the rescued females. Males are quite fertile but mature slower than normal mice.

Figure 9A:
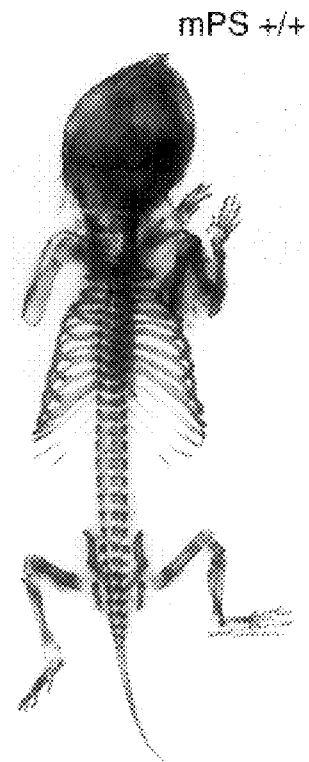
Figure 9B:
Figure 9C:
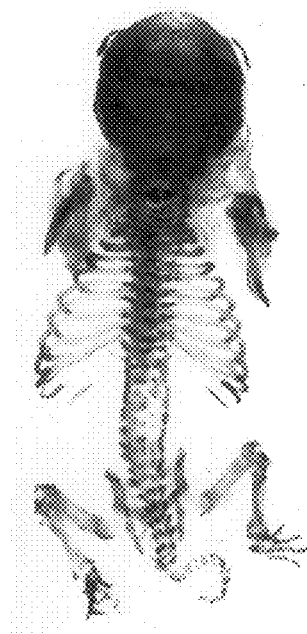

FIG. 9C shows an alcian blue and alizarin red stained skeletal preparation of a rescued newborn animals. The rescued neonate is larger than the null pup and showed vast improvement in cervical and thoracic regions over the knockout mouse (FIGS. 9B, 9C). Wild type vertebral columns normally possess seven cervical vertebrae and thirteen thoracic vertebrae supporting same number of ribs. In null animals, the number of cervical segments was reduced to four to six, with consistent absence of atlas (C-1 vertebra) and frequent fusion of neighboring segments; the number of thoracic segments and ribs were reduced to nine to ten which were again frequently fused.

A cranio-high-caudal-low gradient of rescue effect is evident: the best improvement is seen in the neck region where a complete set of seven cervical vertebrae was restored; the thoracic vertebrae and ribs display similar degree of ossification as the wild type skeleton and were no longer compressed, but it had only eleven segments; the lumbar-tail vertebrae are still disorganized and showed delayed and unsymmetrical ossification, resulting in a split vertebrae and twisted tail. Slower ossification in vertebral column apparently contributed to their slower growth. On hematoxylin and eosin (H&E) stained sections of E15.5 embryos, the defects seen in neck region of the null embryos are completely corrected and no bleeding could be detected, but posterior vertebral defect remained.

The degree of rescue by another wild type transgenic line 17-2 seems to be heterogeneous. Although the majority of the progenies were rescued to a similar degree as compared to line 10-8, others seem to show nearly complete rescue. This heterogeneity may be contributed by the differences in their copy numbers.

B. Mutant Transgene Rescued Mice

Four Thy-1A246E mutant transgenic lines were tested for their ability to rescue the null lethal phenotype of knockout animals. Two of the lines (lines 16-3 and 16-4) yielded similar or better degree of rescue than the lines having wild type human PS1 alleles. The majority of the progeny have only minor tail kink or twist and others are indistinguishable from the wild type murine controls.

Figure 9D:
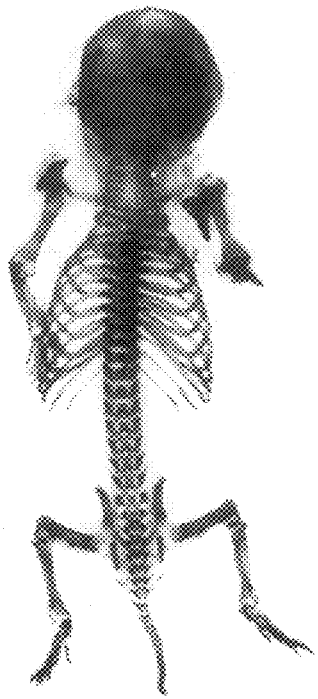

FIG. 9D shows the bone staining of a rescued neonate, heterozygous for the mutant transgene from line 16-3. Comparing with murine wild type skeleton (FIG. 9A), it had correct number of cervical and thoracic vertebrae and normal level of ossification. The structure looks almost completely normal except a minor kink in the tail. A small number of heterozygous line 16-3 rescued mice still display significant vertebral column defects, ranging from missing a rib to crooked posterior segmentation seen on E15.5 embryo sections. Again, no hemorrhage was seen in these rescued mice. The phenotypically well rescued mice are perfectly fertile. Doubling of transgene dosage in line 16-3 increased rescue activity as homozygous mice were phenotypically normal, free of the tail defects present in their heterozygous littermates.

The other two mutant lines (lines 16-1 and 22-1, Table 1) did not rescue the embryonic lethality although they did seem to reduce the severity of the knockout defects. Most transgene-plus null embryos were able to complete gestation and die only after birth. Bone staining showed slightly more ossification and better alignment of the vertebral column than in the non-rescued null pups (not shown). Interestingly, the inheritance of the transgene eliminated CNS hemorrhage from these animals despite little improvement in their axial skeleton. These two lines may have sub-optimal embryonic transgene expression and be regarded as PS1 hypomorphic alleles. The differential correction of hemorrhage and skeleton defects suggest that these animals die of vertebrae deformities instead of hemorrhage.

EXAMPLE 12

Mouse Breeding

The transgenic animals of the present invention can be used to cross breed with transgenic animals overexpressing the human APP containing familial Alzheimer's disease (FAD) mutation (Games, D. et al., Nature 373:523–527 (1995), Hsiao, K et al., Science 274:99–102 (1996)). The resulting mice will express both APP and PS1 with or without FAD mutation on native PS1 null background. The effect of PS1 and PS1FAD mutation on APP processing and β-amyloid peptide (Aβ) production can be studied both in vivo and in vitro. Specifically, the onset and severity of AD-related pathologies can be examined by means of immounhistochemistry. The Aβ levels can be assayed using brain lysate from these animals. In addition, cells from brain tissues or other tissues of the transgenic animals can be cultured in vitro and the potential interactions of APP and PS1 can be investigated in cultured cells. These animals and cultured cells can be used in the assays described below.

EXAMPLE 13

Analysis of Aβ Levels

The animals and cultured cells of the present invention can be used for the study of the expression and processing of APP and the effect of PS1 FAD mutations on expression and processing of APP. Brain Aβ levels were measured from transgenic mice with various combinations of mouse and human PS1 alleles. The results demonstrate that mice expressing the mutant PS1 protein on the murine PS1 null background produce a highly significant increase in the level of Aβ42(43) and the ratio of Aβ42(43)/40, indicating that the FAD mutant protein possesses a deleterious function with regard to Aβ42(43) production that does not require the expression of endogenous wild-type murine PS1. This result indicates that the rescued mouse of this invention and cell lines derived therefrom can serve as model systems for studying this aspect of the etiology of Alzheimer's Disease. The mice and cells can also be used in vivo and in vitro assay systems for the detection and study of compounds that can effect the increase in the level of Aβ42(43) and the ratio of Aβ42(43)/40. Assay systems can be those described herein. In addition, these animals and cells can be used in assays of types known in the art.

Aβ Measurement

Rescue of PS1 null lethality in mice by the human PS1 transgenes allows the analysis of Aβ levels in brains of transgenic mice that have different combinations of human and mouse PS1 alleles, including the humanized PS1 mice where the only PS1 available is of human origin. Mouse Aβ40 and Aβ42(43) levels were measured by the BNT77/BA27 and BNT77/BC05 quantitative sandwich ELISA assays known in the art (Gravina et al., 1995 J. Biol. Chem. 270:7013–7016; Duff et al, 1996) in brain lysates of Thy-PS1 (line 10-8) and Thy-PS1A246E (line 16-3) transgenic mice (3 month of age) in combination with none (PS1−/−), one (PS1+/−) or two (PS1+/+) alleles of endogenous murine PS1. Hemibrains from transgenic mice were homogenized in 70% formic acid. Homogenates were centrifuged at 100,000g for 1 h. The supernatant was recovered, neutralized, and mouse Aβ40 and Aβ42(43) levels were measured.

Several significant findings emerge from this analysis (Table 2): i) Mice heterozygous for the murine PS1 (PS1+/−) produce lower, not higher, levels of both Aβ40 and Aβ42 (43) compared to that of the wild-type controls (Table 2). This finding demonstrates that the effect of PS1 FAD mutations on Aβ42(43) production is not due to a loss of PS1 function; ii) Consistent with published results (Duff et al., 1996; Borchelt et al., 1996, Citron et al., 1997), the amount of Aβ42(43) is increased only when mutant PS1 FAD protein is expressed (Table 2). The most dramatic increase in Aβ42(43)/40 ratio is seen in murine PS1−/−; Thy-PS1A246E genotype, the value of which is 0.394 as compared to the control of 0.163. The increase in the ratio of Aβ42(43)/40 in the hPS1A246E rescued line is caused by both an increase in Aβ42(43) and a concurrent decrease in Aβ40 (Table 2). Since the only PS1 protein produced in this line is the human form PS1A246E, it can be concluded that the increase in Aβ42(43) is associated with this FAD mutation; and iii) Removal of endogenous murine wild-type PS1 seems to reduce the steady state level of Aβ40 since it is significantly: lower in PS1+/− mice and in PS1−/− mice rescued by either the human Thy-PS1 or Thy-PS1A246E transgenes. Direct prove of this concept cannot be obtained, however, since the PS1−/− mice are not viable.

Significant differences in either Aβ40 or Aβ42(43) levels were not detected in mice heterozygous or homozygous for the human PS1 transgenes. In addition, null mice rescued by another mutant line 16-4, whose expression level is comparable to that of the wild-type line 10-8, exhibited a similar increase in brain Aβ42(43) as the rescue mice of the higher expressing line 16-3. These results are consistent with previous reports indicating that differences in the level of transgene expression does not significantly alter the Aβ42 (43) level or Aβ42(43)/40 ratio (Duff et al., 1996; Borchelt et al., 1996; Citron et al., 1997). Therefore, although the PS1 protein is expressed at a lower level in the wild-type Thy-PS1 line 10-8 compared to the Thy-PS1A246E mutant line 16-3, the effect of this difference on Aβ production is not likely to be significant.

PS1 And Aβ Production

It has been reported that expression of the PS1 FAD mutation leads to an increase in the level of Aβ42(43) or the ratio of Aβ42(43)/40 seen in Aβ measurements from fibroblast and plasma samples of PS1 FAD patients, and from transfected cell lines and brains of transgenic mice (Scheuner et al., 1996; Duff et al., 1996; Borchelt et al., 1996, Citron et al., 1997). These reports suggested that the pathogenic mechanism of the PS1 FAD mutations in Alzheimer's disease might involve an increase in Aβ42(43) production. However, the reported results of PS1 FAD effect on Aβ42(43) over-production and on the increase of Aβ42(43)/40 ratio were all obtained in the presence of the endogenous wild-type PS1 alleles. Therefore, it was not truly possible to distinguish whether the mutant effect on Aβ42(43) production results from: 1) a gain of activities by the PS1 FAD proteins in Aβ42(43) production; 2) a partial loss of PS1 function leading to increased Aβ42(43) production; or 3) a dominant negative inactivation of the wild-type PS1 by PS1 FAD proteins, which in essence argues that Aβ42(43) over-production is the result of loss of PS1 function.

The studied conducted according to the present invention and presented herein indicate that all transgenic mouse lines expressing mutant but not wild-type humanPS1, in the presence or absence of the murine wild-type PS1, produce a higher level of Aβ42(43) than control animals. That result indicates that the Aβ42(43) enhancing effect is the intrinsic property of the mutant protein. This result, together with the observations that: i) PS1A246E is functional in developing CNS and other tissues; ii) a 50% reduction in wild-type murine PS1 expression in heterozygous PS1 knockout mice does not lead to an increase in Aβ42(43) production; and iii) that no nonsense or frameshift mutations have been identified in PS1 FAD cases, strongly indicates that the mutation in PS1 FAD results in a gain of function in Aβ42(43) production.

Assessment of activities of PS1 mutants in *C. elegans* yielded somewhat different results. In one reported study, several PS1 FAD mutants, including PS1A46E, were found to be substantially less active than the wild-type protein in compensating sel-12 deficiency (Levitan et al., 1996). This discrepancy in rescue between *C. elegans* and mouse might be attributable to differences in the nature of the defects. For example: unlike the murine PS1 null mutation, a knockout, the *C. elegans* sel-12 mutant is most likely not a complete loss of function mutant. Moreover, the murine somitogenic and *C. elegans* egg chamber differentiation pathways may respond differently to PS1 protein expression. In addition, variability in episomal transgene expression in the *C. elegans* rescue study was not evaluated.

The present results indicate a mild but significant decrease in the steady state levels of Aβ40 and Aβ42(43) in PS1+/− heterozygous mice compared to that of the wild-type controls (Table 2, Aβ40: PS1+/+ 1298 fmoles/g vs. PS1+/− 933 fmoles/g,P<0.02; Aβ42(43): PS1+/+ 211 fmoles/g vs. PS1+/− 144 fmoles/g,P<0.0001). The decrease in Aβ340 occurs also in both the Thy-PS1 and Thy-PS1A246E rescued mice where murine PS1 is replaced by human PS1. The two phenomena may be related and suggest that normal PS1 activity is required for Aβ production.

EXAMPLE 14

Assays

The transgenic animals of the present invention can be used as a source of cells for cell culture. Both animals and cells can be used in assays of this invention. For example, cells of brain tissues lacking a functional native presenilin 1 gene can be cultured using standard culture techniques. Cells having only a functional non-native PS1 gene can also be cultured. The animals and cultured cells can be used as in vivo and in vitro systems for the study of the expression, activity or modulation of PS1 at the genetic or protein level. The animals and cultured cells can be used for the study of the expression, activity or modulation of Notch, Notch ligands and downstream Notch signaling molecules. The animals and cultured cells can also be used for the study of the expression and processing of APP and the effect of PS1FAD mutations on expression and processing of APP.

A study can be designed to screen for a quantitative or qualitative change in an observable aspect of the expression or activity of the non-native PS1. For example, animals cells lacking a functional native PS1 gene and expressing a functional non-native PS1 gene can be used in an assay to screen for compounds that modulate the expression or activity of the non-native PS1. A study can also be designed to screen for compounds that effect, and preferably lower, Aβ production in animals and cells of this invention through modulation of PS1 activity. These compounds can interact with the non-native PS1 protein by virtue of being,e.g., ligands, agonists or antagonists of the protein. The compounds can act directly or indirectly to enhance or decrease the level of transcription of the non-native gene or translation of the non-native RNA. Additionally, the compounds can act through intermediate proteins or ligands that act directly to modulate the expression or activity of the PS1. Many variations of screening methods are known to those of skill in the art and may be applied within the scope of the present invention.

For example, one can conduct a screen to determine the effect of a compound on Aβ production in animals or cells of the present invention. In such screens, the compound is administered to the animals or applied to the medium of cells derived from these animals. The effect of the compound on Aβ production in animals or cells can be compared to the same animals or cells that have not been treated with the compound. Furthermore, the effect of the compound on Alzheimer's disease related markers can be evaluated in animals by means of neuropathological and behavioral analysis.

Therefore, the present invention is shown to provide a model system consisting of transgenic animals, cells and assays that are useful in the study of aspects of the etiology of Alzheimer's Disease, particularly the change in Aβ production seen in conjunction with mutations affecting APP processing. The assays are also useful for screening for compounds that have an effect on Aβ production and for the subsequent study of the compounds.

The foregoing examples describe particular aspects and embodiments of the invention for illustrative purposes and are not limiting on the scope of the invention as recited in the claims below.

What is claimed:

1. A transgenic mouse embryo whose genome is homozygous for a disruption of a native presenilin-1 gene, such that production of functional presenilin-1 is inhibited, and wherein said embryo exhibits abnormal axial skeleton development.

2. A cell line established from a transgenic embryo of claim 1, wherein said production of presenilin-1 in the cells is inhibited.

3. A method for producing a mouse whose genome is heterozygous for a disruption of a native presenilin-1 gene, the method comprising:
   a) providing a DNA sequence which targets and inserts a disruption into a presenilin-1 gene;
   b) introducing said DNA sequence into mouse ES cells;
   c) selecting those mouse ES cells whose genome comprise a disruption of a presenilin-1 gene;
   d) introducing an ES cell selected in step c) in a mouse blastocyst;
   e) transplanting the blastocyst of step d) into a foster mother mouse;
   f) developing the transferred blastocyst to term to produce a chimeric mouse; and
   g) mating chimeric mice to produce a mouse heterozygous for a disruption of the presenillin-1 gene;
wherein said heterozygous mouse expresses mouse presenilin-1 at about 50% of the level of a wild type mouse homozygous for a native presenilin-1 gene.

4. The method of claim 3, wherein said ES cells are introduced in step d) by microinjection.

5. The mouse produced by the method of claim 3.

6. A transgenic mouse whose genome is heterozygous for a disruption of a native presenilin-1 gene, wherein said mouse produces mouse presenilin-1 at about 50% of the level of a wild type mouse homozygous for a native presenilin-1 gene.

7. A cell line established from the transgenic mouse of claim 6, wherein said cells produce mouse presenilin-1 at about 50% of the level of wild type mouse homozygous for a native presenilin-1 gene.

8. The mouse of claim 6, wherein said mouse is fertile, and progeny of the mouse produce mouse presenilin-1 at about 50% of the level of a wild type mouse homozygous for a native presenilin-1 gene.

9. The mouse of claim 8, wherein said disruption has been introduced into the mouse at an embryonic stage by microinjection of mouse ES cells comprising a disruption of a presenilin-1 gene into a mouse blastocyst.

10. A transgenic mouse whose genome comprises a disruption of a native presenilin-1 gene, and wherein said genome further comprises a transgene comprising a DNA sequence encoding a non-native presenilin-1 operably linked to promoter selected from the group consisting of neural and neuronal specific promoters, wherein said mouse is viable, does not produce mouse presenilin-1 and said non-native presenilin-1 is detectable in brain tissue of the mouse.

11. The mouse of claim 10, wherein said non-native presenilin-1 is a human presenillin-1.

12. The mouse of claim 11, wherein said non-native presenilin-1 is selected from the group consisting of wild-type presenilin-1, mutant presenillin-1 and FAD mutant presenilin-1.

13. The mouse of claim 12, wherein said non-native presenilin-1 is the A246E presenilin-1 mutant.

14. The mouse of claim 10, wherein said neuronal specific promoter is the human Thy-1 promoter.

15. The mouse of claim 10, wherein said mouse is hemizygous for the transgene.

16. The mouse of claim 10, wherein said mouse is fertile.

17. The mouse of claim 12, wherein said mouse is hemizygous for a transgene comprising a DNA sequence encoding wild type PS1 or PS1 A246E, wherein said DNA sequence is operably linked to a neuronal specific-promoter.

18. A cell line established from the transgenic mouse claim 10, wherein said genome of said cell comprises a disruption of a native presenilin-1 gene, and wherein said genome further comprises a transgene comprising a DNA sequence encoding a non-native presenilin-1 operably linked to a promoter selected from the group consisting of neural and neuronal specific promoters and wherein said cells do not produce mouse presenilin-1.

19. An assay for determining the effect of a compound on Aβ production comprising:
   a) providing a first and second transgenic mouse whose genomes comprises a disruption of a native presenilin-1 gene, and wherein said genome further comprises a transgene comprising a DNA sequence encoding a non-native mutant presenilin-1 operably linked to promoter selected from the group consisting of neural and neuronal specific promoters, wherein said mouse is viable, does not produce mouse presenilin-1 and said non-native presenillin-1 is detectable in brain tissue of the mouse;
   b) exposing the second mouse to a compound;
   c) incubating both the first and second mice for a period of time;
   d) measuring Aβ production in the brains of both mice; and
   e) comparing the measurements to determine the effect of the compound on Aβ production.

20. An assay for determining the effect of a compound on Aβ production comprising:
   a) providing a first and second population of mouse cells, where the genome of the cells comprise a disruption of a native presenilin-1 gene, and wherein said genome further comprises a DNA construct comprising a DNA sequence encoding an FAD presenilin-1 mutant operably linked to neuronal specific promoter, wherein said cells do not produce mouse presenilin-1;
   b) exposing the second population of cells to a compounds;
   c) incubating both populations of cells for a period of time;
   d) measuring Aβ production in both populations of cells, and e) comparing the measurements to determine the effect of the compound on Aβ production.

21. A method of producing transgenic mice having a transgene comprising a non-native presenilin-1 gene, the method comprising:
   a) providing a transgenic mouse whose genome is heterozygous for a disruption of a native presenilin-1 gene, wherein said mouse expresses mouse presenilin-1 at about 50% of the level of a wild type mouse homozygous for a native presenilin-1 gene;
   b) providing a transgenic mouse whose genome comprises a transgene comprising a DNA sequence encoding a non-native presenilin-1 operably linked to neuronal specific promoter, said non-native presenilin-1 being detectable in brain tissue of the mouse;
   c) breeding said mouse of step a) with the mouse of step b);
   d) producing a transgenic mouse that is heterozygous for a disrupted native presenilin-1 gene and hemizygous for said non-native presenilin-1 gene, wherein said mouse expresses mouse presenilin-1 at about 50% of the level of a wild type mouse homozygous for a native presenilin-1 gene, and wherein said mouse expresses said non native presenilin-1 to a detectable level in brain tissue of the transgenic mouse.

22. The method of claim 21, wherein said transgenic mice of step d) are
   e) bred to produce mice that are hemizygous or homozygous for the DNA sequence encoding a non-native presenilin-1 and are homozygous for the disrupted native presenilin-1 gene.

23. The method of claim 22, wherein said transgenic mice of step d) bred to produce mice that are hemizygous or homozygous for the DNA sequence encoding a non-native presenilin-1 and are homozygous for the disrupted native presenilin-1 gene.

24. The method of claim 23 further comprising:
   f) crossing a mouse produced in step e) with a transgenic mouse expressing a human APP protein to produce a mouse hemizygous or homozygous for expression of a human APP protein, hemizygous or homozygous for said non-native PS1 gene and homozygous for said non-functional mouse PS1 gene, wherein the non-native PS1 is detectable in brain tissue of the mouse.

25. A transgenic mouse hemizygous for a transgene comprising a DNA sequence encoding a human APP protein operably linked to a neural specific promoter, hemizygous for a transgene comprising a DNA sequence encoding a non-native PS1 operably linked to a neural specific promoter and homozygous for non-functional mouse PS1 gene, wherein the non-native PS1 is detectable in brain tissue of the mouse.

26. A transgenic mouse hemizygous for a transgene comprising a DNA sequence encoding a human APP protein operably linked to a neural specific promoter, homozygous for a transgene comprising a DNA sequence encoding a non-native PS1 operably linked to a neural specific promoter and homozygous for a non-functional mouse PS1 gene, wherein the non-native PS1 is detectable in brain tissue of the mouse.

27. A transgenic mouse homozygous for a transgene comprising a DNA sequence encoding a human APP protein operably linked to a neural specific promoter, hemizygous for a transgene comprising a DNA sequence encoding a non-native PS1 operably linked to a neural specific promoter and homozygous for a non-functional mouse PS1 gene, wherein the non-native PS 1 is detectable in brain tissue of the mouse.

28. A transgenic mouse homozygous for a transgene comprising a DNA sequence encoding a human APP protein operably linked to a neural specific promoter, homozygous for a transgene comprising a DNA sequence encoding a non-native PS1 operably linked to a neural specific promoter and homozygous for a non-functional mouse PS1 gene, wherein the non-native PS 1 is detectable in brain tissue of the mouse.

29. The mouse produced by the method of claim 28.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 1:

CCATTGCTCA GCGGTGCTG                                                        19

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 2:

CTGCTGCAGG TGGCTCTGCA                                                       20

(2) INFORMATION FOR SEQ ID NO: 3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 3:

CAGCTCTATA CAAGCAAACA AG                                                    22

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 4:

TAATACGACT CACTATAGGG                                                       20

(2) INFORMATION FOR SEQ ID NO: 5:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 5:

ACGTCGACTC TAGAAGATCT TCGACTCGAG ATCGATGGTA CCCGGGCAGG TTCAAGCTT          60

TGGGATCTCA GTC                                                           73

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 6:

TCATGGTTCT GGGATCTCAG TC                                                 22

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 7:

GTGAAGGAAC CTTATTCTGT GGTG                                               24

(2) INFORMATION FOR SEQ ID NO: 8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 8:

GTCCTTGGGG TCTTCTACCT TTCTC                                              25

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 9:

CTGGAAAGGT CCACTTCGAC TC                                                 22

(2) INFORMATION FOR SEQ ID NO: 10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA -continued (xi) SEQUENCE DESCRIPTION: SEQ ID NO: 10:

TGTGCTTTCT GCATTATACT TGG                                                                23